(12) United States Patent
Hirota

(10) Patent No.: US 8,157,741 B2
(45) Date of Patent: Apr. 17, 2012

(54) ROTATIONAL IMAGING PROBE SAFETY MECHANISM FOR CONDITIONAL ROTATIONAL SPEED REDUCTION

(75) Inventor: Kazuhiro Hirota, Kanagawa (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 1419 days.

(21) Appl. No.: 11/730,064

(22) Filed: Mar. 29, 2007

(65) Prior Publication Data
US 2007/0232892 A1 Oct. 4, 2007

(30) Foreign Application Priority Data

Mar. 31, 2006 (JP) ................................. 2006-099925

(51) Int. Cl.
*A61B 6/00* (2006.01)
(52) U.S. Cl. ......... 600/467; 600/466; 600/118; 600/137
(58) Field of Classification Search .................. 600/407, 600/424, 437, 443–447, 459, 462–463, 466–467, 600/476–480, 118, 137; 128/899
See application file for complete search history.

(56) References Cited

U.S. PATENT DOCUMENTS

| | | | |
|---|---|---|---|
| 5,321,501 A | 6/1994 | Swanson et al. | |
| 5,361,768 A * | 11/1994 | Webler et al. | 600/445 |
| 6,726,675 B1 * | 4/2004 | Beyar | 604/510 |
| 2002/0151799 A1 * | 10/2002 | Pantages et al. | 600/466 |
| 2006/0247529 A1 * | 11/2006 | Rose et al. | 600/466 |

FOREIGN PATENT DOCUMENTS

| | | |
|---|---|---|
| JP | 6-343637 A | 12/1994 |
| JP | 06-343637 A | 12/1994 |
| JP | 2001-79007 A | 3/2001 |
| JP | 2001-079007 A | 3/2001 |

\* cited by examiner

*Primary Examiner* — Brian Casler
*Assistant Examiner* — Rajeev Siripurapu
(74) *Attorney, Agent, or Firm* — Buchanan Ingersoll & Rooney PC

(57) ABSTRACT

An image diagnostic system controls a probe to perform rotational and axially-moving scanning within a body cavity and to acquire reflected signals through the probe. Based on the acquired reflected signals, the system forms and outputs tomographic image of the body cavity and biotissue surrounding the body cavity. The system is provided with a detection unit which detects a direction of movement of the probe in the axially-moving scanning and a control unit which controls the rotational speed of the probe in the rotational scanning. The control unit includes a determination unit which determines whether or not the rotational speed of the probe is to be changed upon detection of movement of the probe toward the distal direction within the body cavity, and changes the rotational speed of the probe upon determination of a change at the determination unit.

20 Claims, 17 Drawing Sheets

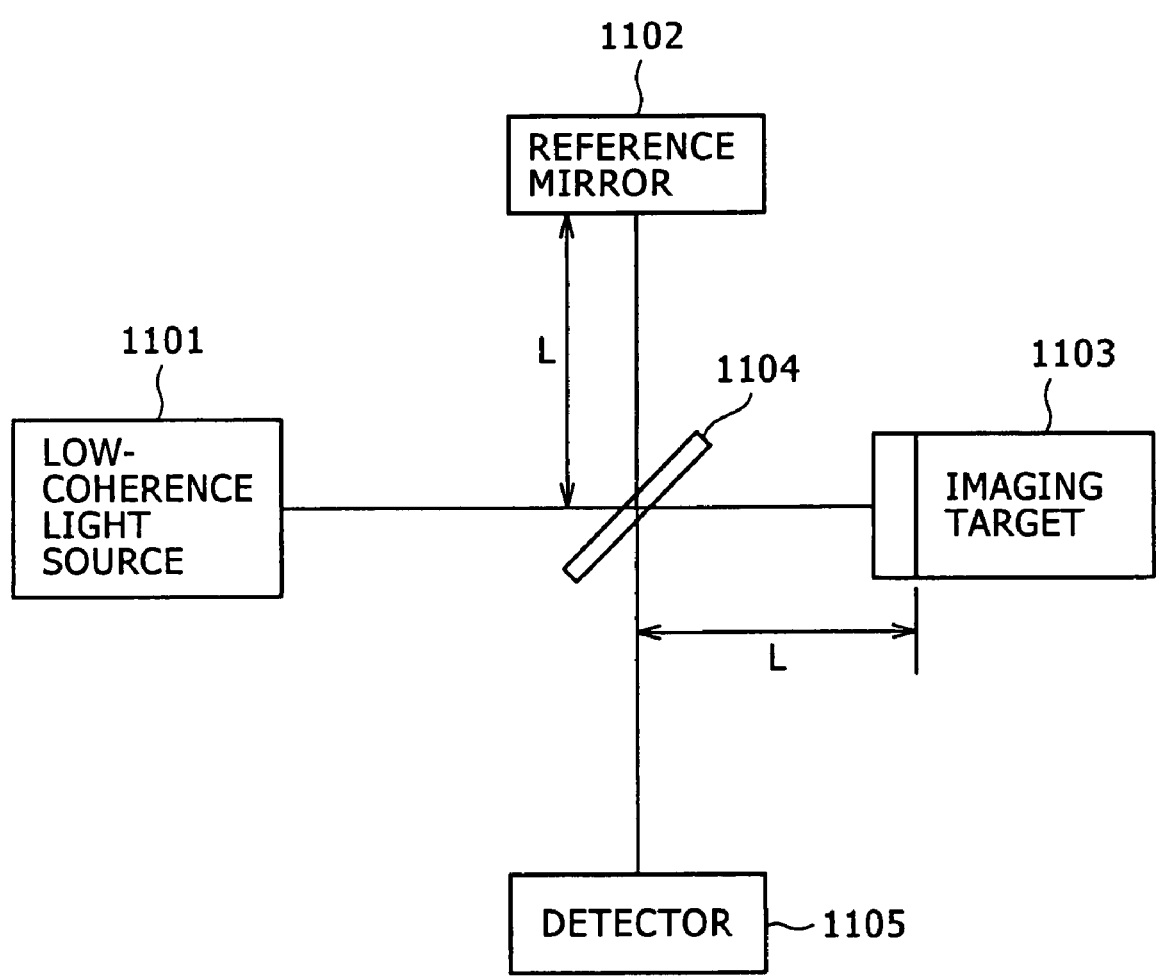

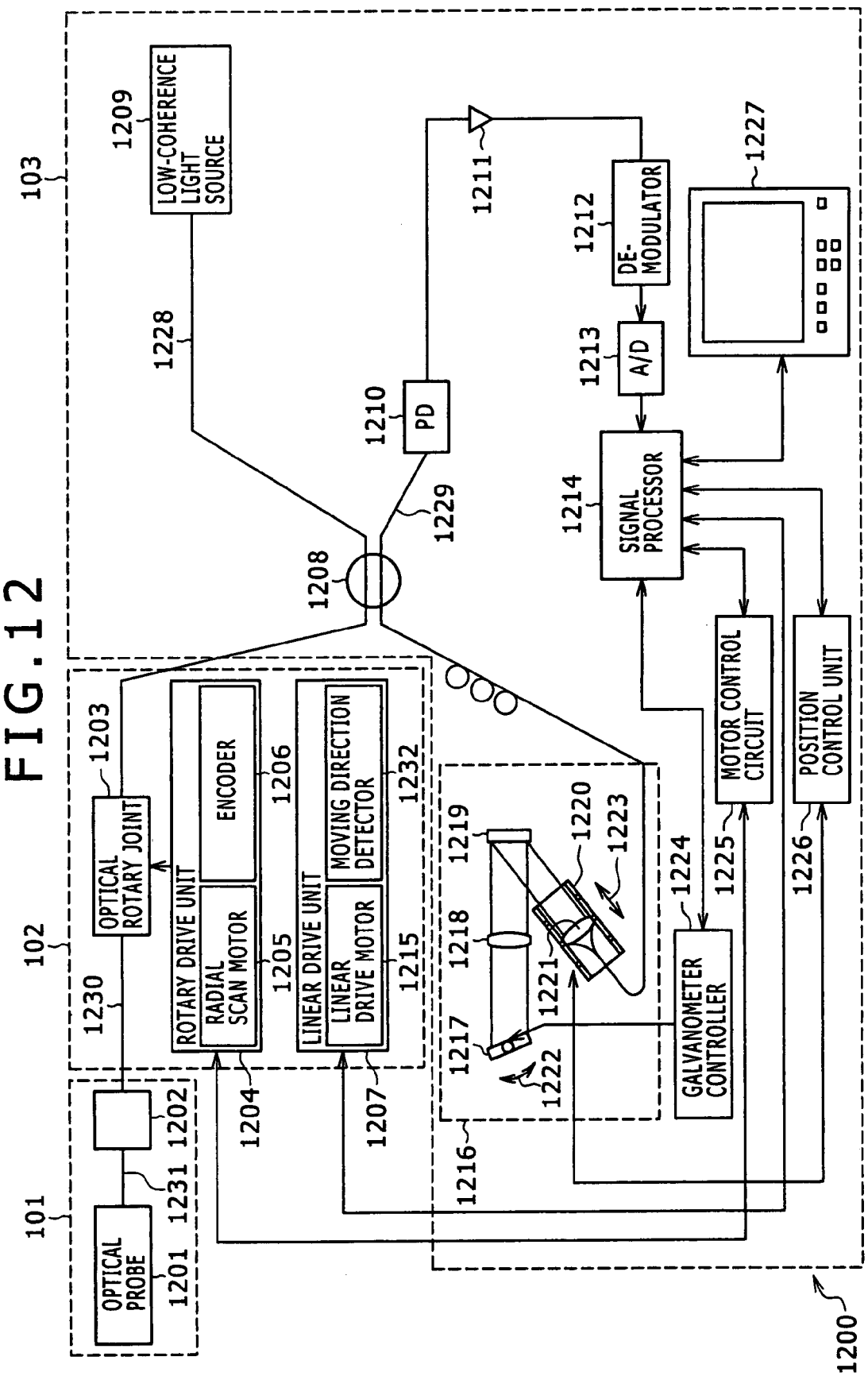

ROTATIONAL IMAGING PROBE SAFETY MECHANISM FOR CONDITIONAL ROTATIONAL SPEED REDUCTION

TECHNICAL FIELD

This invention generally relates to an image diagnostic system and a processing method for such a system.

BACKGROUND DISCUSSION

Image diagnostic systems have been used for diagnosing arteriosclerosis, for preoperative diagnosis upon coronary intervention by a high-performance catheter such as a dilatation catheter (i.e., balloon catheter) or stent, and for assessing postoperative results.

Examples of these image diagnostic systems include intravascular ultrasound (IVUS) imaging systems. In general, the intravascular ultrasound imaging system is constructed to control an ultrasonic transducer to perform radial scanning within a blood vessel, to receive a reflected wave(s) (ultrasound echoes) reflected by biotissue (e.g. the blood vessel wall) by the same ultrasonic transducer, to subject the reflected waves to processing such as amplification and detection, and then to construct and display a tomographic image of the blood vessel on the basis of the intensities of the received ultrasound echoes. An example of such a system is described in JP-A-H06-343637.

In addition to these intravascular ultrasound imaging systems, optical coherence tomography (OCT) imaging systems have been developed in recent years for use as image diagnostic systems. In an OCT imaging system, a catheter with an optical fiber incorporated therein is inserted into a blood vessel. The distal end of the optical fiber is provided with an optical lens and an optical mirror. Light is emitted in the blood vessel while radially scanning the optical mirror arranged on the side of the distal end of the optical fiber, and based on light reflected from biotissue forming the blood vessel, a tomographic image of the blood vessel is then constructed and displayed. An example of this system is described in JP-A-2001-79007.

Improved OCT imaging systems have been proposed in recent years which make use of a wavelength swept light source.

As mentioned above, there are a variety of different image diagnostic systems which use different detection principles. Nonetheless, they are all generally characterized in that a tomographic image (i.e., cross-sectional image) is constructed and displayed by performing radial scanning with a probe. In each of these image diagnostic systems, an increase in axial scanning speed by the realization of faster radial scanning can, therefore, bring about a merit that the time for a diagnosis by the image diagnostic system can be shortened.

However, when a probe is rotated at high speed, for example, as shown in FIG. 9A, when a probe is operated toward the distal direction (i.e., the periphery) within a body cavity with a catheter 11 that is bent at a distal end portion thereof, an ultrasonic transducer unit 12 arranged at the tip of the probe may pierce through the catheter 11, as illustrated in FIG. 9B, thereby breaking the catheter 11 and/or damaging a blood vessel or the like.

As a diagnosis is generally performed by moving a probe toward the user (i.e., in a direction away from the distal direction in the body cavity), such a problem does not typically occur. In some instances, however, a probe may be moved automatically or manually toward the distal direction to finely adjust a measurement-initiating point while confirming tomographic images in real time. Further, with the probe kept rotating, the probe may be moved to a most distal end toward a distal direction to repeat a measurement. When the rotation speed of the probe is fast, such a problem can occur upon movement of the probe toward the distal direction within a body cavity.

SUMMARY

According to one aspect, an image diagnostic system comprises a probe positionable in a body cavity and configured to repeatedly transmit signals into a body cavity and receive reflected signals which are reflected by biotissue surrounding the body cavity, a rotational scanning unit connected to the probe and configured to rotate the probe to perform a rotational scan, an axial-moving unit connected to the probe to axially move the probe, and a control unit configured to produce data based on the reflected signals to construct a tomographic image of the body cavity and surrounding biotissue. The control unit comprises a detection unit configured to detect an axial direction of movement of the probe and a rotational scan controller connected to the rotational scanning unit and configured to control the rotational scanning unit to rotate the probe at a rotational speed. The rotational scan controller controls the rotational scanning unit to change the rotational speed of the probe upon an output from the detection unit.

According to another aspect, an image diagnostic system comprises a probe positionable in a body cavity and configured to repeatedly transmit signals into a body cavity and receive reflected signals which are reflected by biotissue surrounding the body cavity, a radial scan motor connected to the probe to rotate the probe to perform rotational scanning, a linear drive motor connected to the probe to axially move the probe toward a distal direction, a detection unit configured to detect an axial direction of movement of the probe, and means for determining, when the detection unit detects movement of the probe toward the distal direction, whether a rotational speed of the probe is greater than a predetermined value, and for controlling the radial scan motor to reduce the rotational speed of the probe when the rotational speed of the probe is determined to be greater than the predetermined value when the detection unit detects movement of the probe toward the distal direction.

Another aspect involves an image diagnostic apparatus for controlling a probe, which is adapted to be connected to the image diagnostic apparatus and which repeatedly transmits signals into a body cavity which are reflected by biotissue surrounding the body cavity to perform radial scanning within the body cavity. The image diagnostic apparatus comprises a rotational scanning unit connected to the probe and configured to rotate the probe to perform a rotational scan, an axial-moving unit connected to the probe to axially move the probe, and a control unit configured to produce data based on the reflected signals to construct a tomographic image of the body cavity and surrounding biotissue. The control unit comprises a detection unit configured to detect an axial direction of movement of the probe and a rotational scan controller connected to the rotational scanning unit and configured to control the rotational scanning unit to rotate the probe at a rotational speed. The rotational scan controller controls the rotational scanning unit to change the rotational speed of the probe upon an output from the detection unit.

A further aspect involves a method for controlling, in an image diagnostic system, an axially and rotationally movable probe which repeatedly transmits signals within a body cavity and receives signals reflected in the body cavity during rotational scanning, with the signals received by the probe being used to form and output tomographic images of the body cavity and biotissue surrounding the body cavity. The method comprises determining a direction of axial movement of the probe during rotational scanning, and changing a rotational speed of the probe when the probe is determined to be moving toward a distal direction within the body cavity.

Additional aspects a recording medium with a control program stored therein for performing by a computer the method, and the control program.

The system, apparatus and method help reduce the likelihood of the catheter being broken when the rotation of the probe is made fast during radial scanning.

BRIEF DESCRIPTION OF THE DRAWING FIGURES

The foregoing and additional aspects of the disclosed system and method will become more apparent from the following detailed description considered with reference to the accompanying drawing figures briefly described below.

FIG. 11 is a block diagram illustrating the basic principle of the OCT imaging system.

FIG. 12 is a block diagram depicting features and aspects of the OCT imaging system.

DETAILED DESCRIPTION

[First Embodiment]
1. General Overall Construction of IVUS Imaging System

Figure 1:
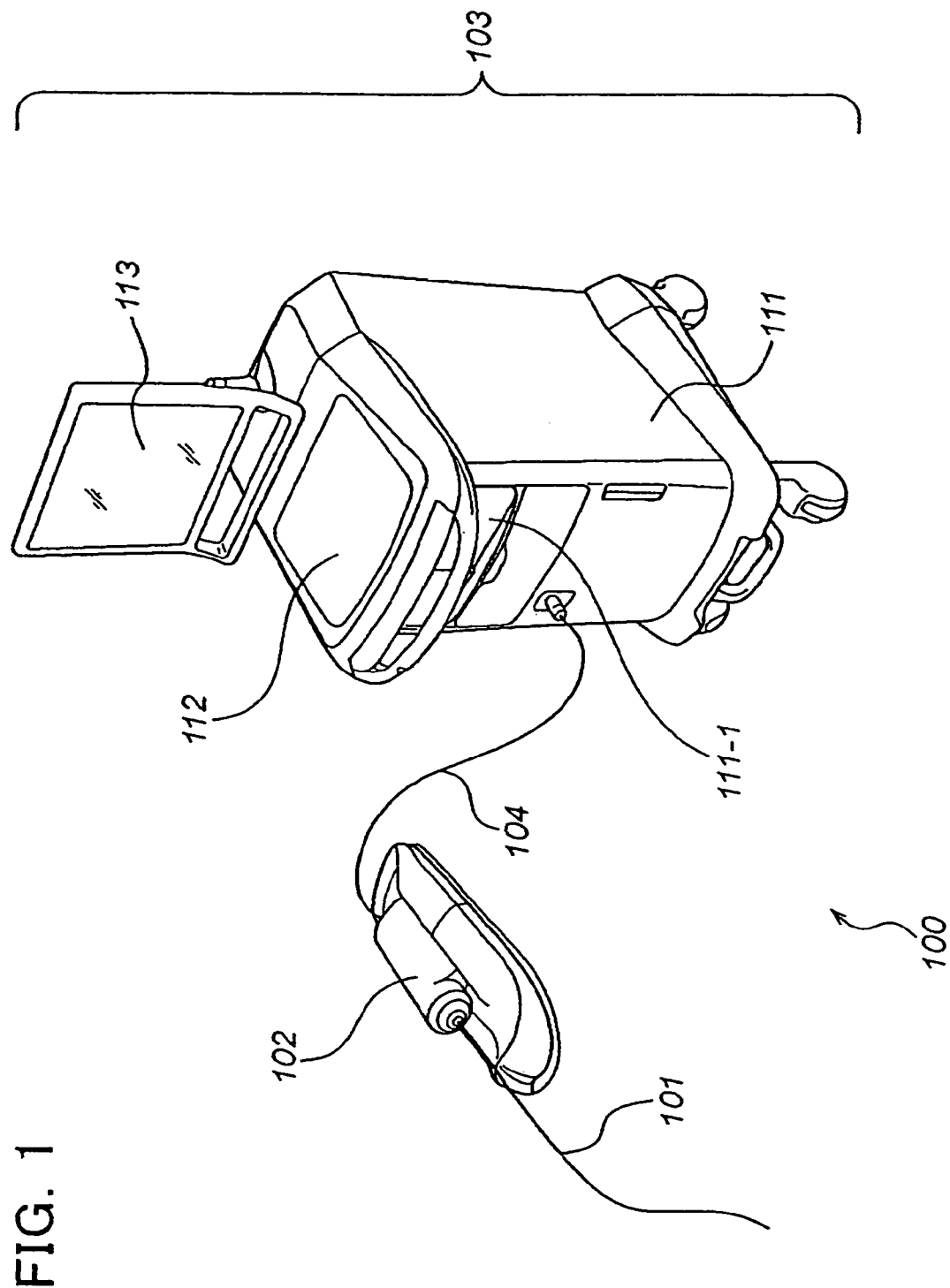
FIG. 1 is a perspective view showing features and aspects of an IVUS imaging system according to a first embodiment disclosed herein.

Regarding to FIG. 1, an intravascular ultrasound (IVUS) imaging system (i.e., image diagnostic system) 100 according to one illustrated and disclosed embodiment includes a catheter section (i.e., probe) 101, a scanner & pull-back unit 102 and an operation control system 103. The scanner & pull-back unit 102 and the operation control system 103 are connected together via a signal line 104 and compose an image diagnostic apparatus.

Figure 4:
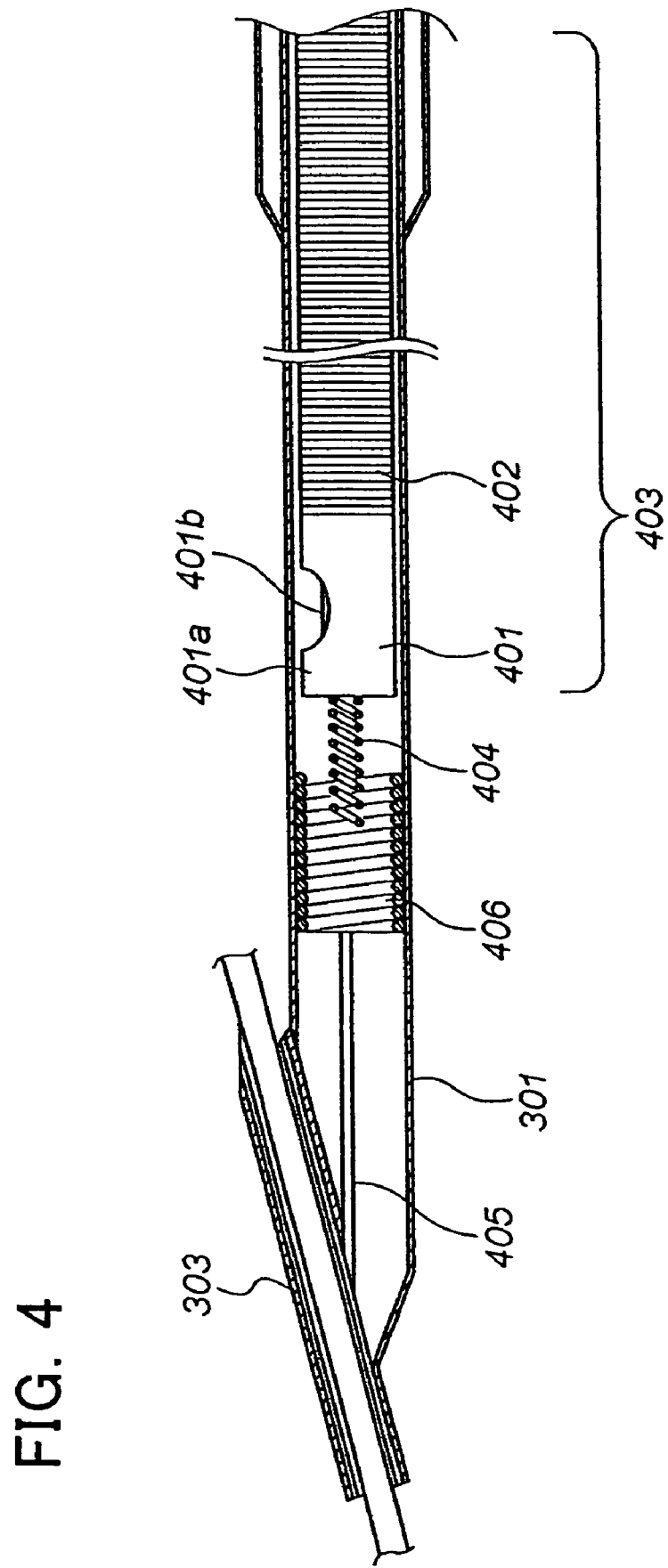
FIG. 4 is a cross-sectional view of the distal end portion of the catheter section shown in FIG. 3.

The catheter section 101 is adapted to be inserted directly into a blood vessel to measure internal conditions of the blood vessel by way of an ultrasonic transducer which is shown in FIG. 4. The scanner & pull-back unit 102 is composed of the integrated combination of the scanner unit (i.e., the rotational scanning unit) and the pull back unit (i.e., the axially-moving unit). The scanner & pull-back unit 102 controls movements of the ultrasonic transducer within the catheter section 101.

The operation control system 103 operates to input various preset values upon performing an intravascular ultrasound diagnosis to also process data acquired by a measurement and to display them as a tomographic image.

The operation control system 103 includes a main control unit 111 which performs processing of data acquired by a measurement and outputs the results of the processing, and a printer/DVD recorder 111-1 which prints the results of the processing in the main control unit 111 or records (i.e., stores) them as data.

The operation control system 103 also includes a control panel 112. Through the control panel 112, a user is able to input various values such as preset values. In addition, the operation control system 103 includes an LCD monitor 113 (i.e., display) which displays the results of the processing in the main control unit 111.

2. Aspects and Features of IVUS Imaging System

Figure 2:
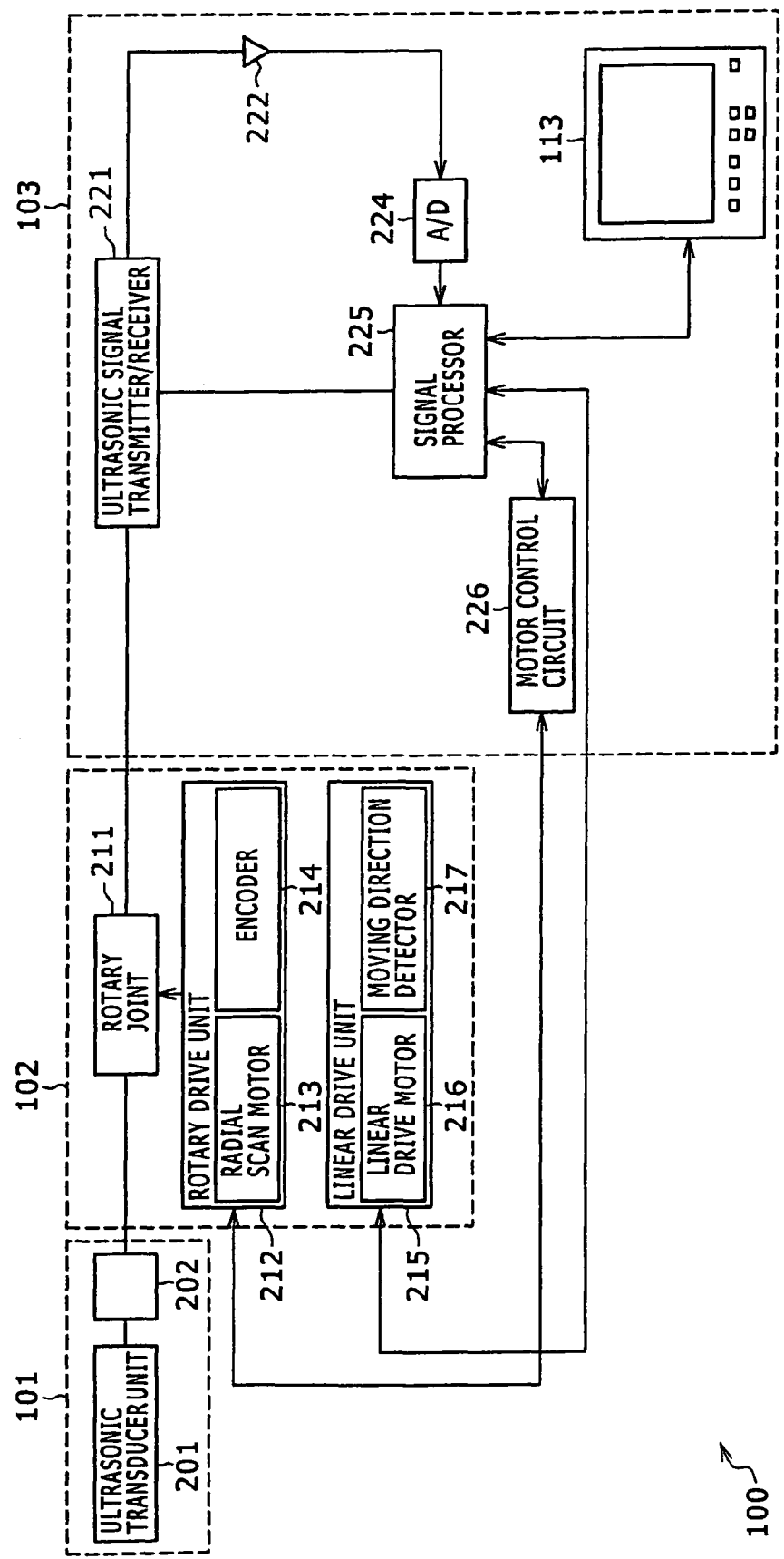
FIG. 2 is a block diagram schematically illustrating additional aspects and features of the IVUS imaging system.

FIG. 2 schematically illustrates in more detail aspects and features of the IVUS imaging system 100 illustrated in FIG. 1. The distal end of the catheter section 101 is internally provided with an ultrasonic transducer unit 201. With the distal end of the catheter section 101 inserted within a blood vessel, the ultrasonic transducer 201, responsive to a pulse wave transmitted by an ultrasonic signal transmitter/receiver 221, transmits ultrasound in the direction of a section of the blood vessel, and receives the reflected signals (echoes) and transmits them as ultrasonic echo signals to the ultrasonic signal transmitter/receiver 221 via a connector 202 and a rotary joint 211.

The scanner & pull-back unit 102 includes the rotary joint 211, a rotary drive unit 212 and a linear drive unit 215. The ultrasonic transducer unit 201 within the catheter section 101 is rotatably mounted by the rotary joint 211, which connects a non-rotatable block and a rotatable block with each other, and is rotationally driven by a radial scan motor 213. Rotation of the ultrasonic transducer unit 201 in a circumferential direction within the blood vessel makes it possible to detect ultrasound echo signals required for the construction of a tomographic image of the blood vessel at the predetermined position within the blood vessel.

The operation of the radial scan motor 213 is controlled based on a control signal transmitted from a signal processor 225 via a motor control circuit 226. Further, each rotation angle of the radial scan motor 213 is detected by an encoder 214. Each output pulse outputted at the encoder 214 is inputted in the signal processor 225, and is used as a timing for the reading of signals to be displayed.

The scanner & pull-back unit 102 includes the linear drive unit 215 and, based on an instruction from the signal processor 225, specifies movements (axial movements) of the catheter section 101 in the direction of its insertion (in the directions toward and away from the distal direction within a body cavity). Axial movement is achieved by the operation of a linear drive motor 216 on the basis of a control signal from the signal processor 225. Further, the moving direction of the catheter section 101 in its axial movement (toward or away from the distal direction within the body cavity) is detected by a moving direction detector (i.e., detection unit) 217, and the result of the detection is inputted to the signal processor 225.

The radial scan motor 213 and the linear drive motor 216 may be detachably connected together or may be integrally constructed. Axial movements by the linear drive motor 216 can be achieved by a ball screw or the like. Further, the moving direction detector 217 can be realized, for example, by mounting an encoder on the linear drive motor 216. Namely, the moving direction of the catheter section 101 in its axial movement can be detected by detecting the direction of rotation of the linear drive motor 216.

The ultrasonic signal transmitter/receiver 221 is provided with a transmission circuit and a reception circuit (not shown). Based on a control signal transmitted from the signal processor 225, the transmission circuit transmits a pulse wave to the ultrasonic transducer unit 201 in the catheter section 101.

The reception circuit, on the other hand, receives the signals based on ultrasonic echoes from the ultrasonic transducer unit 201 in the catheter section 101. The thus-received the signals are amplified by an amplifier 222.

At an A/D converter 224, the signals outputted from the amplifier 222 are sampled to produce digital data (ultrasound echo data) for one line.

Ultrasound echo data produced in line units at the A/D converter 224 are inputted into the signal processor 225. The signal processor 225 detects the ultrasound echo data, constructs tomographic images of the blood vessel at respective positions within the blood vessel, and outputs them at a predetermined frame rate to the LCD monitor 113.

3. Construction of Control Panel 112

Figure 8:
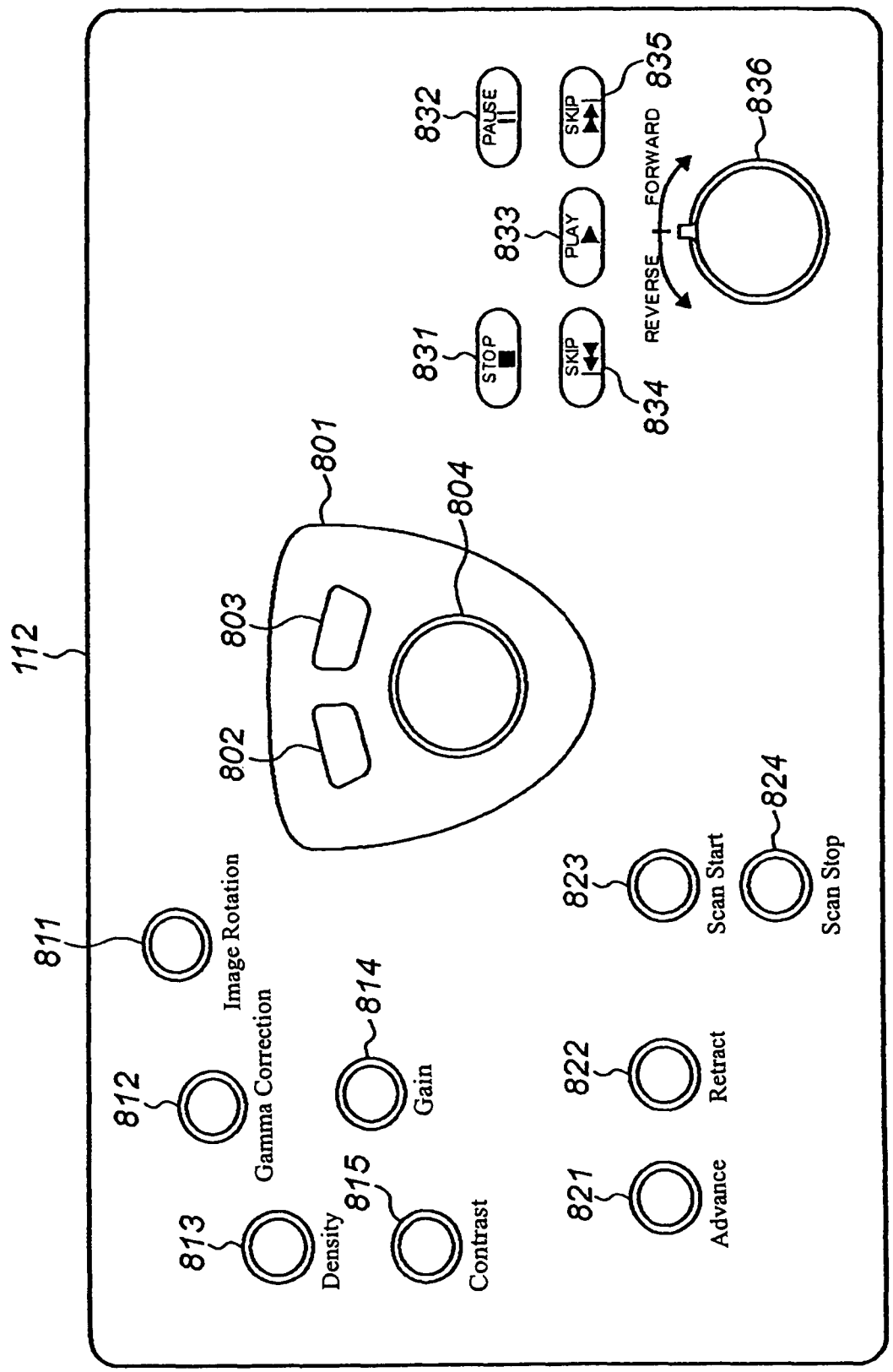
FIG. 8 is a plan view of a control panel used in the IVUS imaging system.
Figure 9A:
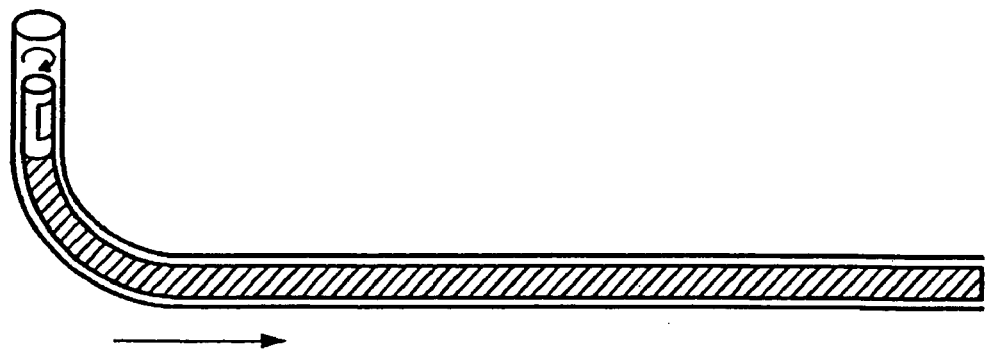
FIGS. 9A and 9B are schematic views illustrating difficulties that can arise during operation of the probe rotating at a high speed.
Figure 9B:
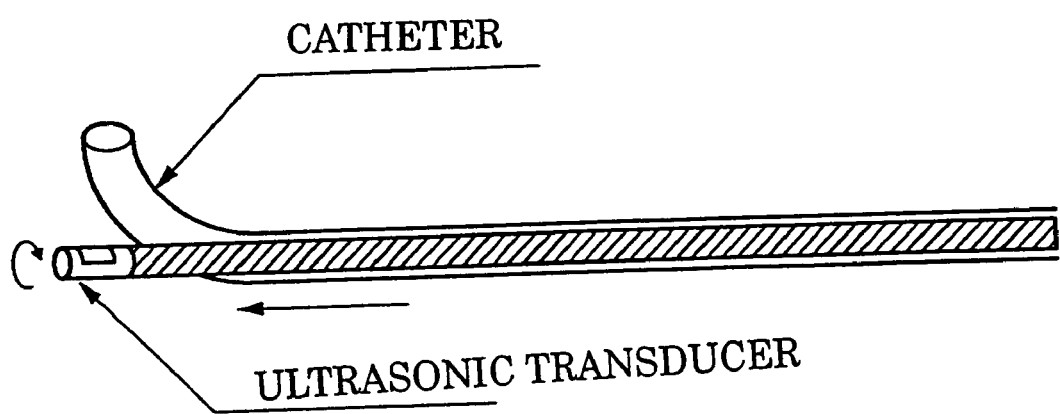

FIG. 8 is a plan view illustrating one example of the construction of the control panel 112. A LCD monitor control unit (monitor control portion) 801 controls various images to be displayed on the LCD monitor 113. A trackball 804 is used to control a pointer displayed on the LCD monitor 113, and left and right click buttons 802, 803 are provided for the trackball. The setting of various conditions (for example the rotational speed) in a diagnosis is effected via the LCD monitor control portion 801.

The control panel 112 also includes setting dials (i.e., knobs) 811-815 for setting correction values upon processing ultrasound echo data at the signal processor 225. The image rotation setting dial 811 sets an amount of rotation for rotating a tomographic image produced based on inputted ultrasound echo data. The gamma correction setting dial 812 is used to finely adjust the gamma value to perform color matching. The density setting dial 813 adjusts the density of the tomographic image to be displayed. The gain setting dial 814 adjusts a gain for ultrasound echo data to be inputted. The contrast setting dial 815 adjusts the contrast of the tomographic image to be displayed.

The control panel 112 additionally includes buttons 821-824 to be used upon performing axially-moving scanning by the ultrasonic transducer unit 201 in the catheter section 101. While the advance button 821 is being pressed, the linear drive motor 216 continues to operate so that the ultrasonic transducer unit 201 in the catheter section 101 moves toward the distal direction within the body cavity. When the pressing of the advance button 821 is cancelled, the movement stops. While the retract button 822 is being pressed, the linear drive motor 216 continues to operate so that the ultrasonic transducer unit 201 in the catheter section 101 moves away from distally within the body cavity (i.e., in the direction toward the user). When the pressing of the retract button 822 is cancelled, the movement stops.

When the scan start button 823 is pressed, the ultrasonic transducer unit 201 in the catheter section 101 rotates at a predetermined rotational speed. When the scan stop button 824 is pressed, the rotating ultrasonic transducer unit 201 is stopped.

The control panel 112 further includes several buttons 831-835 and a dial 836 which are to be used upon displaying stored tomographic images on the LCD monitor 113. The PLAY button 833 is used to playback stored tomographic images at a predetermined frame rate on the LCD monitor 113. The STOP button 831 is used to stop the playback of tomographic images. The PAUSE button 832 is used to temporarily pause the playback of tomographic images under display at a predetermined frame rate.

The skip-up button 834 is operated to jump up to a tomographic image at a predetermined position from a tomographic image currently being displayed (to a tomographic image at a backward position from a tomographic image currently under display). The skip-down button 835 is used to jump down to a tomographic image at a predetermined position from a tomographic image currently under display (to a tomographic image at a forward position from a tomographic image currently under display).

When the fast forward/reverse playback dial 836 is rotated clockwise, tomographic images are displayed forward at a higher frame rate than a predetermined frame rate. When the fast forward/reverse playback dial 836 is rotated counter-clockwise, on the other hand, tomographic images are displayed backward at a higher frame rate than a predetermined frame rate.

With the above-described control panel 112, radial scanning by the ultrasonic transducer unit 201 is realized by controlling different control buttons and dials to perform axial movements and rotation, respectively. The system, apparatus and method disclosed here are not, however, limited to the disclosed and illustrated details of the control panel. For example, an extra control button may be arranged to directly realize radial scanning. On the other hand, each axial movement may be realized by directly pressing the corresponding control button or by directly moving the scanner & pull-back unit 102 forward or backward by hand. Even in such a modification, the moving direction of each axial movement can be similarly detected by the moving direction detector 217.

Figure 3:
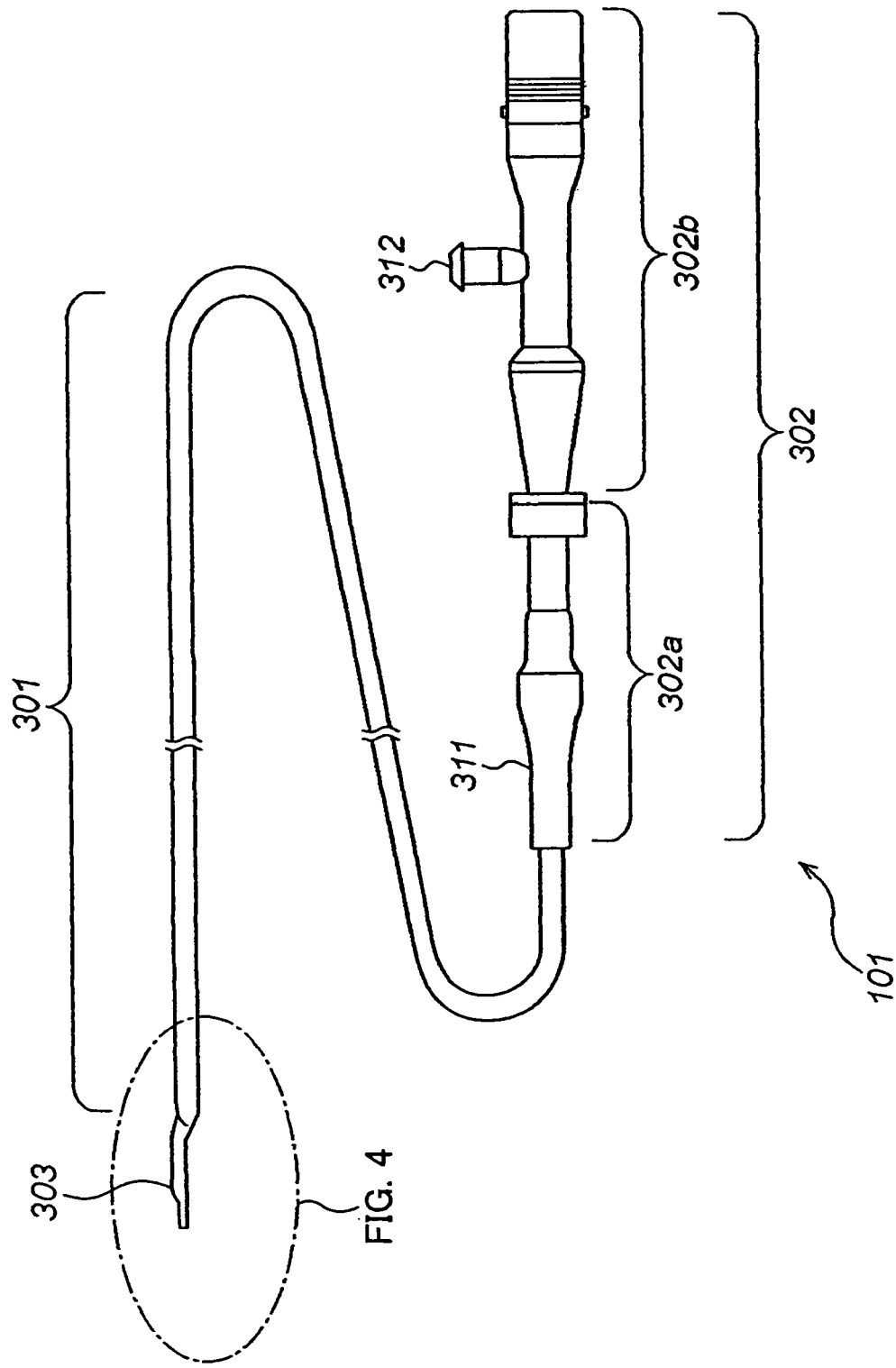
FIG. 3 is a perspective view illustrating the overall construction of a catheter section in the IVUS imaging system.

4. Construction of Catheter Section 4.1 Overall Construction of Catheter Section The overall general construction of the catheter section 101 is illustrated in FIG. 3. The catheter section 101 is constructed of an elongated catheter sheath 301 adapted to be inserted into a blood vessel and a connector 302, not inserted into the blood vessel, that is arranged on the side of the user's hand to permit handling and operation by the user. A guidewire lumen 303 is provided at the distal end of the sheath 301. Within the catheter sheath 301 is a lumen which continuously extends from a connecting portion with the guidewire lumen 303 to a connecting portion with the connector 302.

The connector 302 is composed of a sheath connector 302a and a driveshaft connector 302b. The sheath connector 302a is constructed integrally with the proximal end of the catheter sheath 301. The driveshaft connector 302b is arranged on the proximal end of a driveshaft, which will be described subsequently herein, to rotatably hold the drive shaft.

The anti-kink protector 311 is arranged at a boundary portion between the sheath connector 302a and the catheter sheath 301. The arrangement of this anti-kink protector 311 makes it possible to maintain a predetermined degree of stiffness, thereby preventing any short tight twist or curl which might otherwise be caused by a sudden change in torque. The driveshaft connector 302b is provided with an injection port 312 to which a syringe (not illustrated) or the like can be attached to fill up the lumen of the catheter sheath 301 in its entirety with an ultrasound transmission fluid. The proximal end of the driveshaft connector 302b is constructed to be connected to the scanner & pull-back unit 102.

4.2 Construction of the Distal End Portion of Catheter Section

FIG. 4 illustrates in more detail the distal end portion of the catheter section 101. Through the lumen of the catheter sheath 301, an imaging core 403 extends over substantially the entire length of the catheter sheath 301. The imaging core 403 is provided with an ultrasonic transducer unit 401 for transmitting and receiving ultrasound and also includes the driveshaft 402 for transmitting drive force to rotate the ultrasonic transducer unit 401. The ultrasonic transducer unit 401 is comprised of an ultrasonic transducer 401b and a housing 401a in which the ultrasonic transducer 401b is held. Ultrasound is transmitted from the ultrasonic transducer 401b toward the surrounding biotissue of a body cavity, and reflected waves from the surrounding biotissue of the body cavity are received at the ultrasonic transducer 401b.

The driveshaft 402 is constructed in the form of a coil, accommodates a signal line therein, and extends from the ultrasonic transducer 401b to the connector 302.

The ultrasonic transducer 401b possesses a rectangular or circular shape, and is formed by depositing electrodes on opposite sides of a piezoelectric member made of PZT or the like. The ultrasonic transducer 401b is arranged to assume a position around the central axis of rotation to prevent the driveshaft 402 from causing rotational fluctuations.

The housing 401a is in the form of a short cylindrical tube provided at a part thereof with a cut-off portion. Examples of materials forming the housing 401a include metal or hard resin. Examples of methods for forming the housing 401a include machining such as cutting, laser machining or pressing a tubular material to form the cut-off portion, or the desired shape may be directly obtained by injection molding, MIM (metal injection molding) or the like. The housing 401a carries the ultrasonic transducer 401b therein. The proximal end side of the housing 401a is connected with the driveshaft 402. On the distal end side of housing 401a, a resilient member 404 in the form of a short coil is arranged.

The resilient member 404 is coil-shaped wire which can be produced by forming a stainless steel wire into a coiled shape. The arrangement of the resilient member 404 on the distal end side of the housing 401a provides the imaging core 403 with improved stability upon rotation. Gold plating can be applied to a surface of the resilient member 404 or the housing 401a. As gold is a metal having high x-ray opacity, the gold plating permits visualization of the resilient member 404 in an image taken by an x-ray imaging system when the catheter sheath 301 is inserted into a body cavity. As a consequence, the user can easily ascertain the position of the ultrasonic transducer 401b.

At a boundary portion between the distal end portion of the catheter sheath 301 and the guidewire lumen 303, a discharge channel 405 is arranged to discharge out the ultrasound transmission fluid injected during priming.

A reinforcement coil 406 is arranged inside the catheter sheath 301 to assist in preventing kinking of the distal end portion of the catheter sheath 301.

The guidewire lumen 303 has a bore adapted to receive a guidewire. The guidewire is inserted beforehand in a body cavity and is utilized to guide the catheter sheath 301 to a diseased part.

The driveshaft 402 is constructed of a multiple or multilayer, tight coil or the like having properties such that it can rotate and slide relative to the catheter sheath 301, is flexible, and can relatively smoothly transmit rotation. The multiple or multilayer, tight coil or the like may be made, for example, of a wire of a metal such as stainless steel.

Owing to the rotation of the driveshaft 402, the lumen can be observed over 360 degrees. To perform an observation over a still greater range, it is only necessary to slide the driveshaft 402 in the axial direction.

Figure 5:
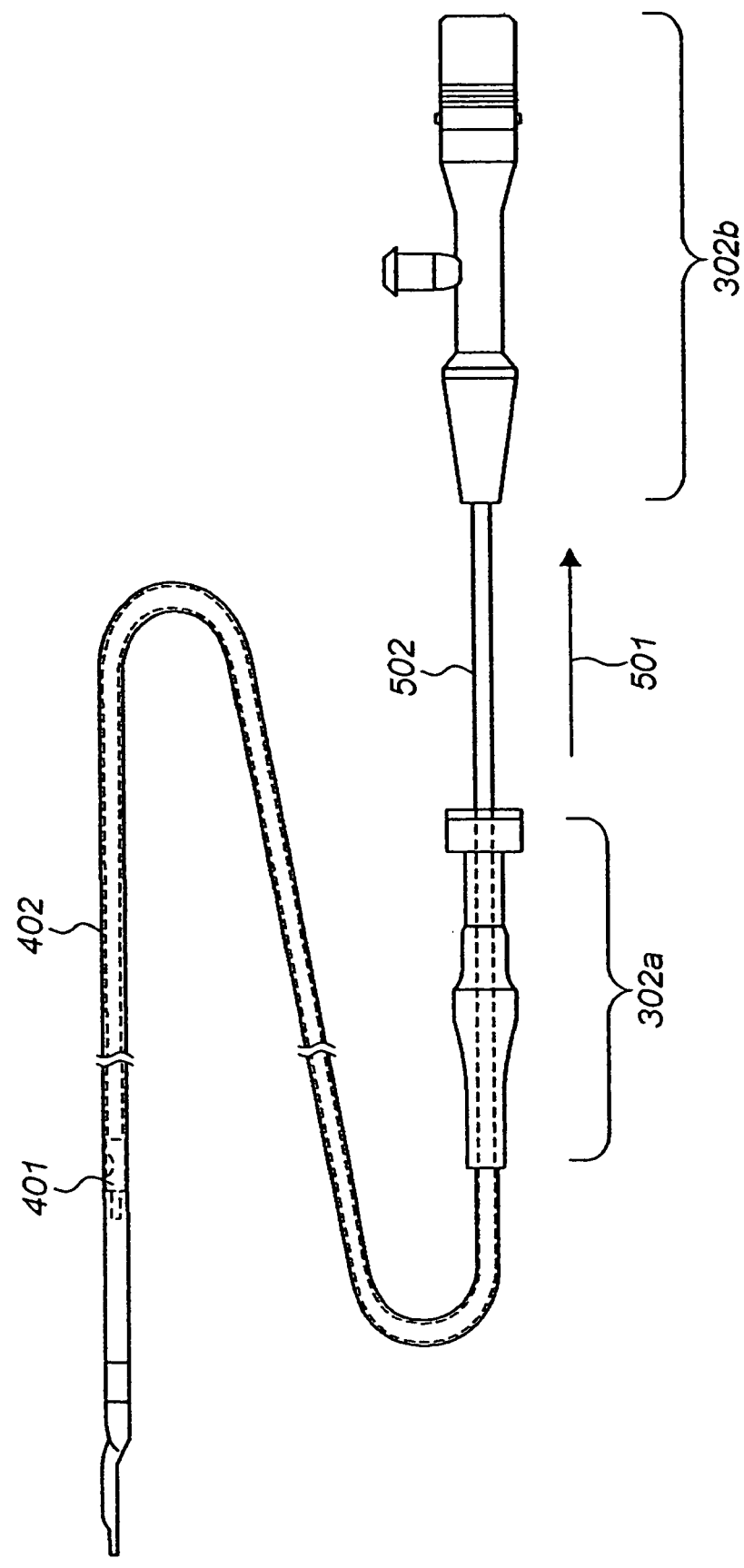
FIG. 5 is a schematic view of the catheter section showing the manner of sliding a driveshaft relative to a catheter sheath in the catheter section.

FIG. 5 schematically illustrates the manner in which the driveshaft 402 is slidably advanced relative to the catheter sheath 301. The sliding of the driveshaft connector 302b toward its proximal end (in the direction of arrow 501) with the sheath connector 302a held fixed causes the driveshaft 402, which is accommodated within and fixed to the driveshaft connector 302b, and the ultrasonic transducer unit 401, which is fixedly secured on the distal end of the driveshaft 402, to also slide in the axial direction. This axial sliding may be effected either manually by the user or by an electrical drive. On the distal end side of the driveshaft connector 302b, a protecting inner tube 502 is arranged to avoid exposure of the driveshaft 402 which rotates at a high speed.

Figure 6A:
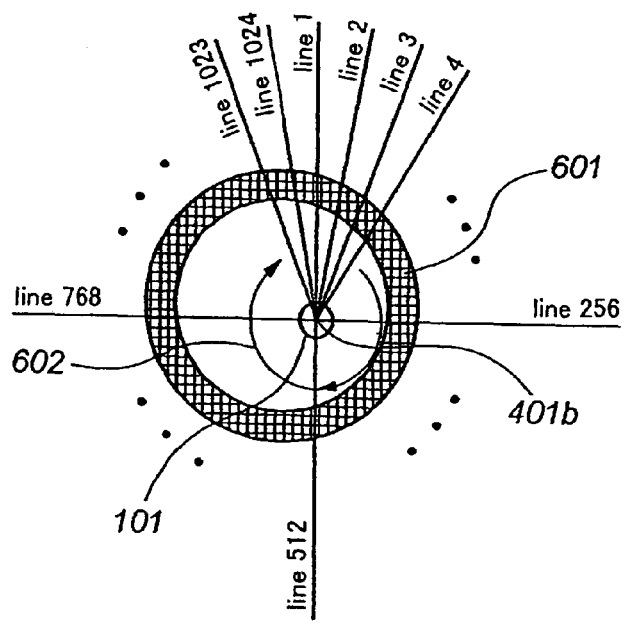
FIGS. 6A and 6B are perspective views in cross-section of a blood vessel and the catheter section inserted therein, illustrating movements of the catheter section during an intravascular ultrasound diagnosis.
Figure 6B:
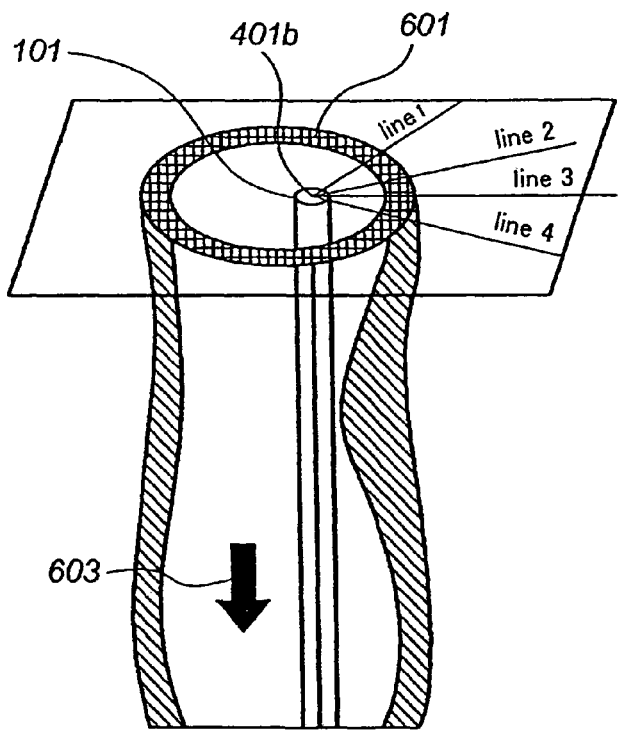

5. Operation of the Catheter Section 101 Upon Intravascular Ultrasound Diagnosis FIGS. 6A and 6B schematically illustrate movements of the catheter section 101 during an intravascular ultrasound (IVUS) diagnosis. FIG. 6A shows a section of a blood vessel 601 in which the catheter section 101 has been inserted. As described above, the ultrasonic transducer 401b is internally mounted at the distal end of the catheter section 101, and is rotated in the direction of arrow 602 by the radial scan motor 213.

From the ultrasonic transducer 401b, the transmission/reception of ultrasound is performed at respective rotation angles. Lines 1, 2, . . . , 1024 indicate the transmitting directions of ultrasound at the respective rotation angles. In this embodiment, 1,024 transmissions/receptions are intermittently performed while the ultrasonic transducer 401b rotates over 360 degrees in a predetermined blood vessel section 601. The number of transmissions/receptions of ultrasound during 360-degree rotation is not limited specifically to 1,024, but can be set as desired. The scanning that is repeated with the transmission/reception of signals while rotating the ultrasonic transducer (signal transmission/reception device) as described above is generally called "radial scanning" or "rotational scanning".

The transmissions/receptions of ultrasound are performed while advancing the catheter through the blood vessel in the direction of arrow 603 shown in FIG. 6B.

6. Processing at the Signal Processor 225

Figure 7:
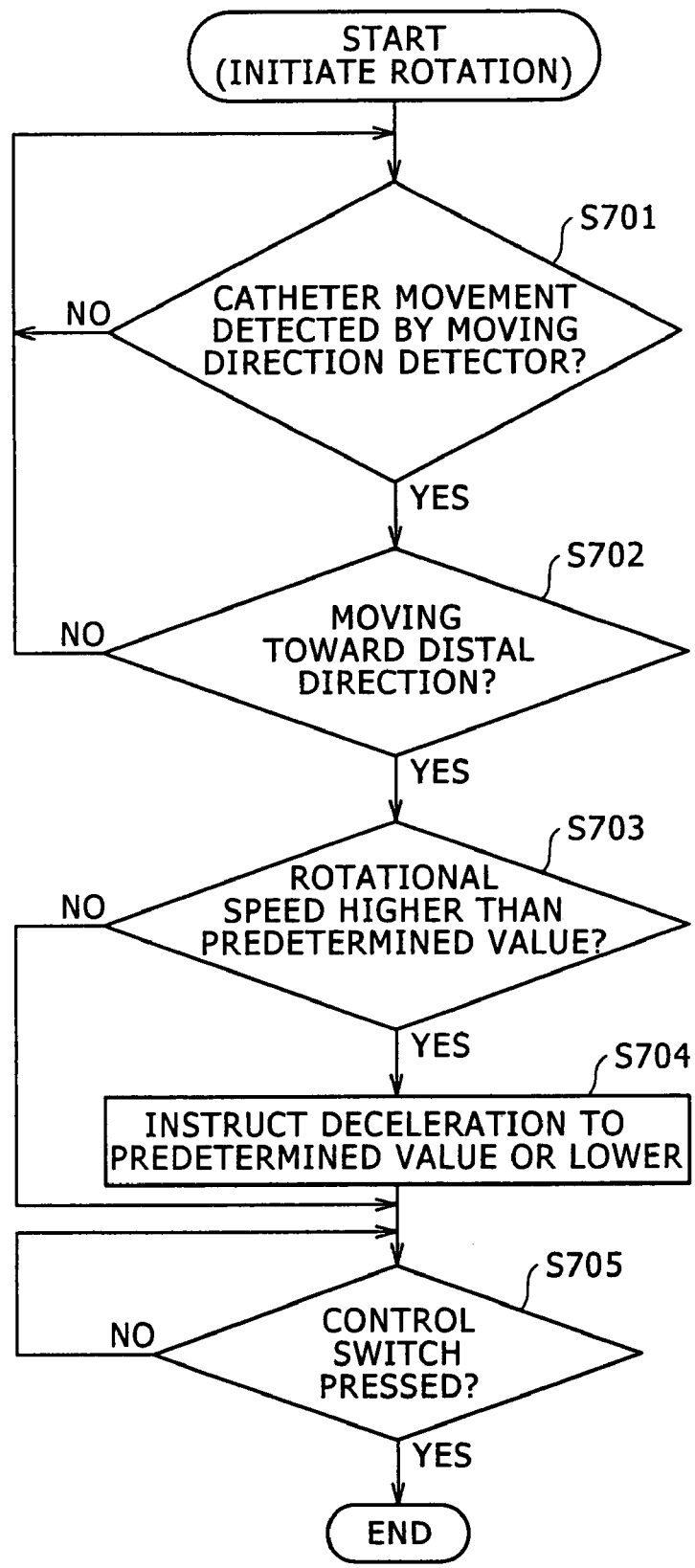
FIG. 7 is a flow chart illustrating operational aspects of processing at a signal processor when an ultrasonic transducer has initiated rotation.

When the ultrasonic transducer unit 201 initiates rotation at a predetermined rotational speed, the processing shown in FIG. 7 is started. That is, the flow chart shown in FIG. 7 illustrates the operational aspects of the signal processor 225 when the ultrasonic transducer unit 201 has initiated rotation.

When the processing is started responsive to the receipt of a press signal (button operation signal) from the scan start button 823, a determination is made on the basis of an output signal from the moving direction detector 217 in step S701 as to whether or not the ultrasonic transducer unit 201 has moved axially. If no axial movement is determined, the process remains in a stand-by mode until an axial movement is detected.

If an axial movement is determined in step S701, the process advances to step S702. In step S702, a determination is made as to whether or not the axial movement is a movement toward the distal direction within the body cavity. If the axial movement is not determined to be a movement toward the distal direction within the body cavity (in other words, is determined to be a movement away from distally), the process returns to step S701.

On the other hand, if the axial movement is determined to be a movement toward the distal direction within the body cavity, the process advances to step S703. In step S703, it is determined whether or not the rotational speed of the ultrasonic transducer unit 201 is higher than a predetermined value. The rotational speed of the ultrasonic transducer unit 201 is determined by referring to a value preset via the control panel 112 before pressing the scan start button 823. As an alternative, it may also be determined based on an actually-measured value of the rotational speed as calculated on the basis of an output from the encoder 214. It is to be assumed that the predetermined value is set, for example, at 1,800 rpm.

If the rotational speed of the ultrasonic transducer unit 201 is not determined to be higher than the predetermined value in step S703, the process advances to step S705. If the rotational speed is determined to be higher than the predetermined value, on the other hand, that is, if the preset value of the rotational speed is set at a high speed (for example, 3,600 rpm), the process advances to step S704, and a deceleration instruction is transmitted to the rotary drive unit 212 via the motor control circuit 226 such that the rotational speed is reduced to or lower than the predetermined value. Responsive to the receipt of the deceleration instruction, the rotary drive unit 212 performs control such that the rotary speed of the ultrasonic transducer unit 201 is reduced to or lower than the predetermined value.

In step S705, a determination is made as to whether or not another control button (dial) is pressed (turned). If no other control button (dial) is determined to be pressed (turned) in step S705, the process remains in a stand-by state until another control button (dial) is pressed (turned). If another control button (dial) is determined to be pressed (turned), on the other hand, the processing shown in FIG. 7 is ended.

If it is determined in step S705, for example, that the advance button 821 has been pressed, the ultrasonic transducer unit 201 is moved again toward the distal direction. If the retract button 822 is determined to have been pressed, the ultrasonic transducer unit 201 is moved away from distally (in a direction opposite the distal direction). If the scan start button 823 is determined to have been pressed, the rotational speed of the ultrasonic transducer unit 201 is caused to return to the preset rotational speed (the rotational speed higher than the predetermined value). When the scan stop button 824 is pressed, the rotation of the ultrasonic transducer unit 201 which is rotating at a rotational speed equal to or higher than the predetermined value is stopped.

In the above description, the signal processor 225 transmits to the rotary drive unit 212 the deceleration instruction such that the rotational speed is reduced to or lower than the predetermined value. However, the disclosed system and method are not limited to such an operation. A stop instruction may be transmitted to stop the rotation.

From the above-description, it is thus seen that the system and apparatus include means (e.g., signal processor 225) for determining, when movement of the probe toward the distal direction is detected, whether the rotational speed of the probe is greater than a predetermined value, and for effecting appropriate control to reduce the rotational speed of the probe when the rotational speed of the probe is determined to be greater than the predetermined value when the probe is determined to be moving toward the distal direction.

The IVUS imaging system according to this embodiment makes it possible to help avoid the possibility of breakage of a catheter. That is, in the event the rotational speed of the probe is relatively high during radial scanning at a time when the probe is moved toward the distal direction, the rotational speed of the probe is decelerated to a speed at which there is less likelihood, or no likelihood, for the occurrence of a catheter breakage problem, or the rotation of the probe is stopped.

[Second Embodiment]

The description set forth above concerning the first embodiment describes processing at the signal processor when the radial scanning by the ultrasonic transducer is made faster in a IVUS imaging system. However, the disclosed system and method are not limited specifically to IVUS imaging systems. Indeed, the disclosure herein is also applicable to other image diagnostic systems. The description which follows describes application of the disclosed subject matter to an optical coherence tomography (OCT) imaging system.

1. Measurement Principle of the OCT Imaging System

For background purposes, set forth below is a general description of the diagnostic principle of the OCT imaging system. Because light is electromagnetic radiation, it generally has the property that beams of light interfere with each other when they are superimposed. The interference property defining whether light interferes readily or hardly is called "coherence." In general OCT imaging systems, low-coherence light (i.e., short-coherence light) of low interference property is used.

Figure 10A:
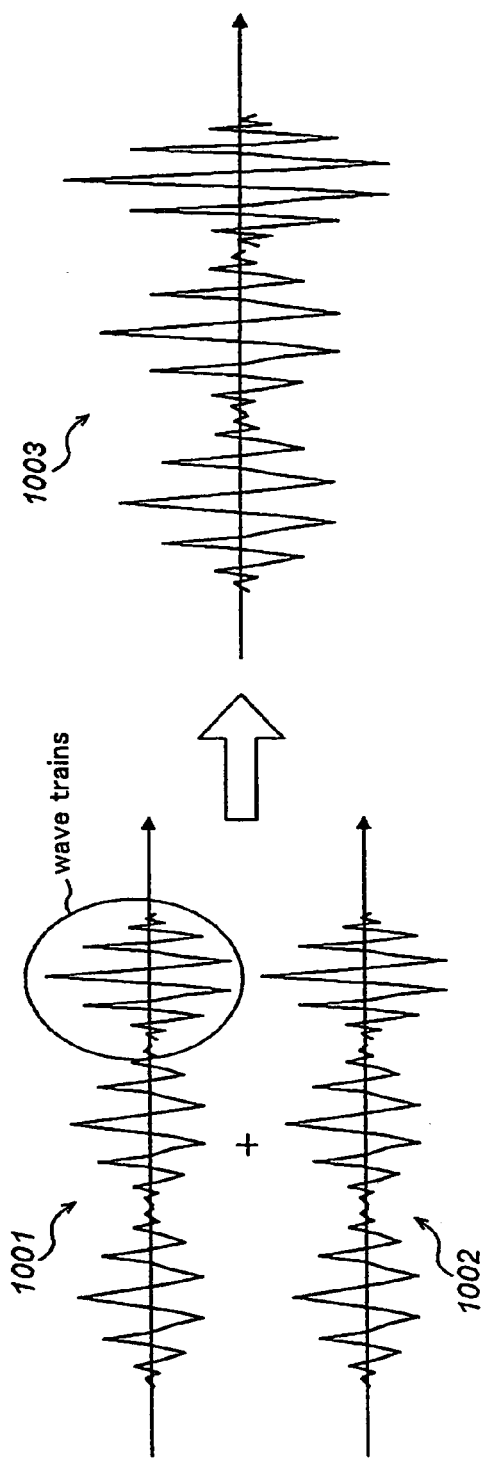
FIGS. 10A and 10B are waveform diagrams illustrating the principle of a measurement by an OCT imaging system according to a second embodiment of the present invention.
Figure 10B:
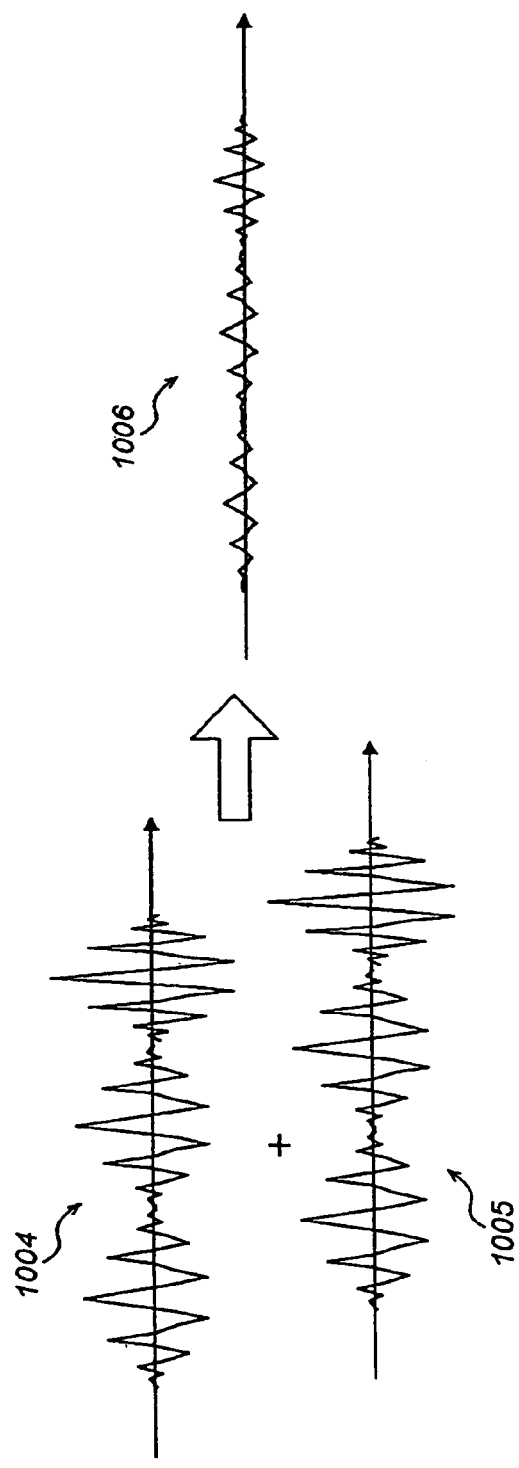

Referring to FIG. 10A, when time is plotted along the abscissa and electric field is plotted along the coordinate, low-coherence light becomes random signals as indicated at 1001 and 1002. Individual peaks in the figure are called "wave trains", and have their own, mutually-independent phases and amplitudes. When the same wave trains (1001 and 1002) overlap with each other as in FIG. 10A, the wave trains interfere with each other to intensify each other as represented at 1003. On the other hand, when there is a slight delay in time between wave trains (1004 and 1005 in FIG. 10B), the wave trains cancel each other so that no interference light is observed as represented at 1006 in FIG. 10B.

The OCT imaging system makes use of these properties, and the basic principle of the system is illustrated in FIG. 11. As illustrated, light emitted from a low-coherence light source 1101 is split into a reference path and a sampling path at a beam splitter 1104. One of the resulting light beams which is split into the reference path is then directed toward a reference mirror 1102 and another resulting light beam which is split into the sampling path is then directed toward an imaging target (i.e. blood vessel wall) 1103. At this time, reflected light returning from the imaging target includes light reflected on the surface of the imaging target, light reflected at shallow points in the imaging target, and light reflected at deep points in the imaging target.

As the incident light is low-coherence light, the reflected light on which interference can be observed is, however, only the reflected light from a reflection surface located at a position apart by a distance of $L+\Delta L/2$ from the beam splitter 1104, where L represents the distance from the beam splitter 1104 to the reference mirror 1102 and ΔL represents a coherence length.

By changing the distance from the beam splitter 1104 to the reference mirror 1102, it is possible to selectively detect at a detector 1105 only reflected light from a reflection surface, which corresponds to the thus-changed distance, in the imaging target. A tomographic image can then be constructed by visualizing internal structural information of the imaging target on the basis of the intensities of reflected light beams corresponding to such respective distances.

2. General Overall Construction of the OCT Imaging System

The general overall construction of the OCT imaging system is similar to that of the IVUS imaging system described above and shown in FIG. 1 and so a detailed description of the construction is not repeated.

3. Aspects and Features of the OCT Imaging System

FIG. 12 illustrates features and aspects associated with the OCT imaging system (i.e. image diagnostic system) 1200 according to this illustrated and disclosed embodiment. The system includes a low-coherence 1209 light source such as an ultra-high intensity, light emitting diode. The low-coherence light source 1209 outputs low-coherence light having a wavelength around 1,310 nm, and the outputted low-coherence light shows interference property only in such a short distance range that its coherence length approximately ranges from several micrometers to over tens of micrometers.

When the light is split into two and the resulting beams of light are combined back, the combined light is, therefore, detected as coherent light when the difference between the two optical path lengths from the splitting point to the combining point falls within a short distance range around 17 μm, but no coherent light is detected when the difference in optical path length is greater than the above-described range.

The light from the low-coherence light source 1209 impinges on a proximal end face of a first single mode fiber 1228, and is transmitted toward its distal end face. At an optical coupler 1208 arranged midway along the first single mode fiber 1228, the first single mode fiber 1228 is optically coupled with a second single mode fiber 1229. Therefore, the light transmitted through the first single mode fiber 1228 is split into two by the optical coupler 1208 and the resulting two beams of light (i.e., the sample path and the reference path) are transmitted further.

On the more distal end side of the first single mode fiber 1228 than the optical coupler 1208, an optical rotary joint 1203 is arranged to connect a non-rotatable block and a rotatable block with each other such that light can be transmitted.

Further, an optical-probe connector 1202 is detachably connected to a distal end of a third single mode fiber 1230 in the optical rotary joint 1203. Via the connector 1202, the light from the low-coherence light source 1209 is transmitted to a fourth single mode fiber 1231 which is inserted in an optical probe (i.e., catheter) 1201 and is rotationally drivable.

The transmitted light is irradiated from the distal end side of the optical probe 1201 toward a surrounding biotissue of a body cavity while performing radial scanning. A portion of reflected light scattered on a surface or interior of the biotissue is collected by the optical probe 1201, and returns to the side of the first single mode fiber 1228 through the reverse optical path. A portion of the thus-collected, reflected light is transferred by the optical coupler 1208 toward the second single mode fiber 1229, and is introduced into a photodetector (for example, photodiode 1210) from an end of the second single mode fiber 1229. It is to be noted that the rotatable block side of the optical rotary joint 1203 is rotationally driven by a radial scan motor 1205 of a rotary drive unit 1204.

Further, rotation angles of the radial scan motor 1205 are detected by an encoder 1206. The optical rotary joint 1203 is provided with a linear drive unit 1207 which, based on an instruction from a signal processor 1214, controls movement (axial movement) of the catheter section 101 in the direction of its insertion (toward or away from a periphery within a body cavity). An axial movement is realized by an operation of a linear drive motor 1215 on the basis of a control signal from the signal processor 1214. Further, the moving direction of the catheter section 101 in its axial movement (toward or away from distally within the body cavity) is detected by a moving direction detector 1232, and the result of the detection is inputted to the signal processor 1214.

It is to be noted that the radial scan motor 1205 and the linear drive motor 1215 may be detachably connected together or may be integrally constructed. Axial movements by the linear drive motor 1215 can be realized by a ball screw or the like. Further, the moving direction detector 1230 can be realized, for example, by mounting an encoder on the linear drive motor 1215. Namely, the moving direction of the catheter section 101 in its axial movement can be detected by detecting the direction of rotation of the linear drive motor 1215.

On the more distal end side of the second single mode fiber 1229 than the optical coupler 1208, an optical path length (OPL) varying mechanism 1216 is arranged to vary the optical path length of reference light.

This OPL varying mechanism 1216 is provided with a first OPL varying means for varying the optical path length, which corresponds to the examinable range in the direction of the depth of the biotissue, at high speed and also with a second OPL varying means for varying the optical path length by a length equivalent to a variation in the length of a new optical probe to absorb the variation when the new optical probe is used as a replacement (so generally intravascular probes are disposable for infection prevention).

Opposing the distal end of the second single mode fiber 1229, a grating (diffraction grating) 1219 is arranged via a collimator lens 1221 which is mounted together with the distal end of the second single mode fiber 1229 on a single axis stage 1220 and is movable in the direction indicated by arrow 1223. Further, a galvanometer mirror 1217 which is rotatable over small angles is mounted as the first OPL varying means via the grating 1219 and an associated lens 1218. This galvanometer mirror 1217 is rotated at high speed in the direction of arrow 1222 by a galvanometer controller 1224.

The galvanometer mirror 1217 serves to reflect light by its mirror, and functions as a reference mirror. The galvanometer mirror 1217 is constructed such that its mirror mounted on a movable part of its galvanometer is rotated at high speed by applying an a.c. drive signal to the galvanometer.

Described more specifically, by applying a drive signal to the galvanometer from the galvanometer controller 1224 and rotating the galvanometer at high speed in the direction of arrow 1222 with the drive signal, the optical path length of reference light is varied at high speed by an optical path length equivalent to an examinable range in the direction of the depth of the biotissue. A single cycle of variations in optical path length (single scanning) becomes a cycle that acquires interference light data for a single line (in line unit).

On the other hand, the single axis stage 1220 forms the second OPL varying means having a variable OPL range just enough to absorb a variation in the optical path length of a new optical probe when the optical probe 1201 is replaced by the new (i.e., another) optical probe. In addition, the single axis stage 1220 is also able to function as an adjustment means for adjusting an offset. Even when the distal end of the optical probe 1201 is not in close contact with a surface of the biotissue, for example, the optical probe can still be set in such a state as interfering from a position on the surface of the biotissue by slightly varying the optical path length with the single axis stage 1220.

The light varied in the optical path length by the OPL varying mechanism 1216 is combined with the light, which has escaped from the side of the first single mode fiber 1228, at the optical coupler 1208 arranged midway along the second single mode fiber 1229, and the combined light is received at the photodiode 1210.

The light received at the photodiode 1210 is performed photoelectric conversion and amplified by an amplifier 1211, and is then inputted into a demodulator 1212. At the demodulator 1212, demodulation processing is performed to extract only the signal portion of the interfered light, and the output of the demodulator 1212 is inputted into an A/D converter 1213.

At the A/D converter 1213, interference light signals are sampled as much as for 200 points to produce digital data (interference data) for one line. The sampling frequency is a value obtained by dividing with 200 the time required for a single scan of the optical path length.

The interference light data in the line unit, which have been produced at the A/D converter 1213, are inputted into the signal processor 1214. At this signal processor 1214, the interference light data in the direction of the depth are converted into video signals to constitute tomographic images at respective positions in the blood vessel. These tomographic images are then outputted at a predetermined frame rate to an LCD monitor 1227.

The signal processor 1214 is connected with a position control unit 1226. The signal processor 1214 performs control of the position of the single axis stage 1220 via the position control unit 1226. In addition, the signal processor 1214 is also connected with a motor control circuit 1225 to control rotational drive by the radial scan motor 1205.

Further, the signal processor 1214 is also connected with the galvanometer controller 1224 which controls the scanning of the optical path length of the reference mirror (galvanometer mirror). The galvanometer controller 1224 outputs a drive signal to the signal processor 1214, and based on this drive signal, the motor control circuit 1225 is synchronized with the galvanometer controller 1224.

4. Construction of Catheter Section

Figure 13:
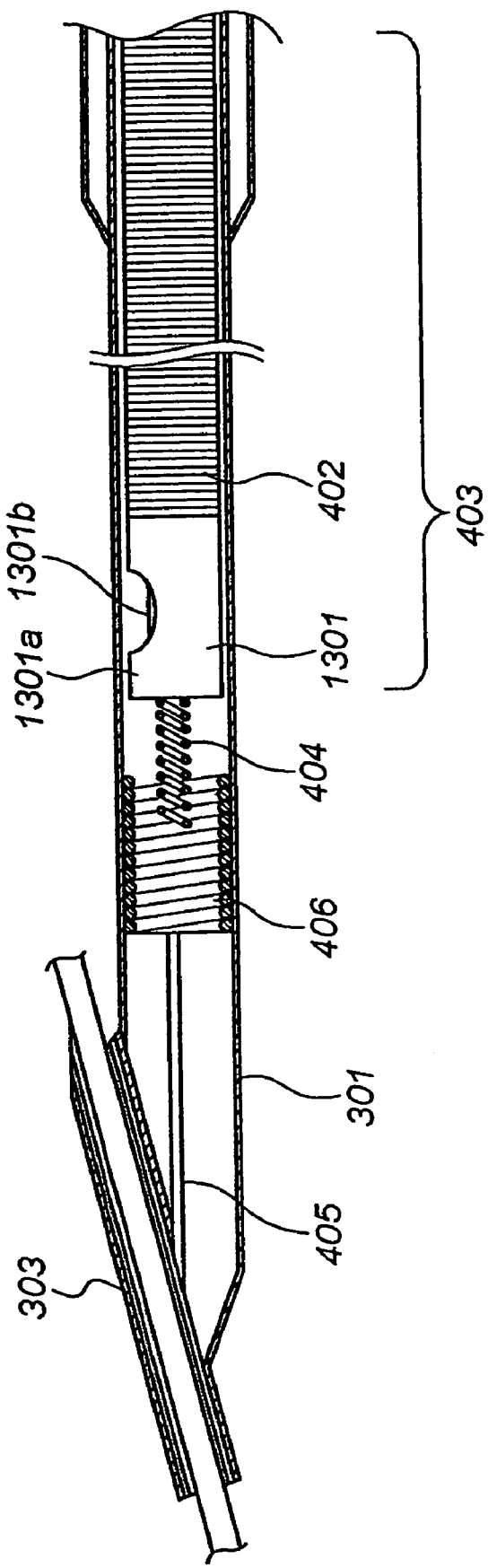
FIG. 13 is a cross-sectional view of the distal end portion of a catheter section used in the OCT imaging system.

The overall construction of the catheter section 101 in the OCT imaging system is the same as the overall construction of the catheter section in the IVUS imaging system described above and so a detailed description of such overall construction is not repeated here. With reference to FIG. 13, the following describes differences associated with the construction of the distal end portion of the catheter section 101 in the OCT imaging system 1200.

An optical probe 1301 which irradiates/receives low-coherence light is arranged within the lumen of the catheter sheath 301. The optical probe 1301 is provided with a prism or mirror 1301b to perform lateral irradiation. The optical probe 1301 includes the prism or mirror 130 1b and a housing 1301a in which is held the prism or mirror 1301b. The optical probe 1301 irradiates low-coherence light toward a surrounding biotissue of a body cavity from the prism or mirror 1301b, and at the prism or mirror 1301b, receives reflected light from the surrounding biotissue of the body cavity.

An optical fiber is disposed through the drive shaft 402, and extends from the housing 1301a to the connector 1202. As the advance injection of physiological saline (priming work) is not absolutely needed in the OCT imaging system according to this embodiment, the priming discharge channel 405 formed at the boundary portion between the distal end portion of the catheter sheath 301 and the guidewire lumen 303 in the IVUS imaging system described above may be omitted.

5. Processing by the Signal Processor 1214

Figure 14:
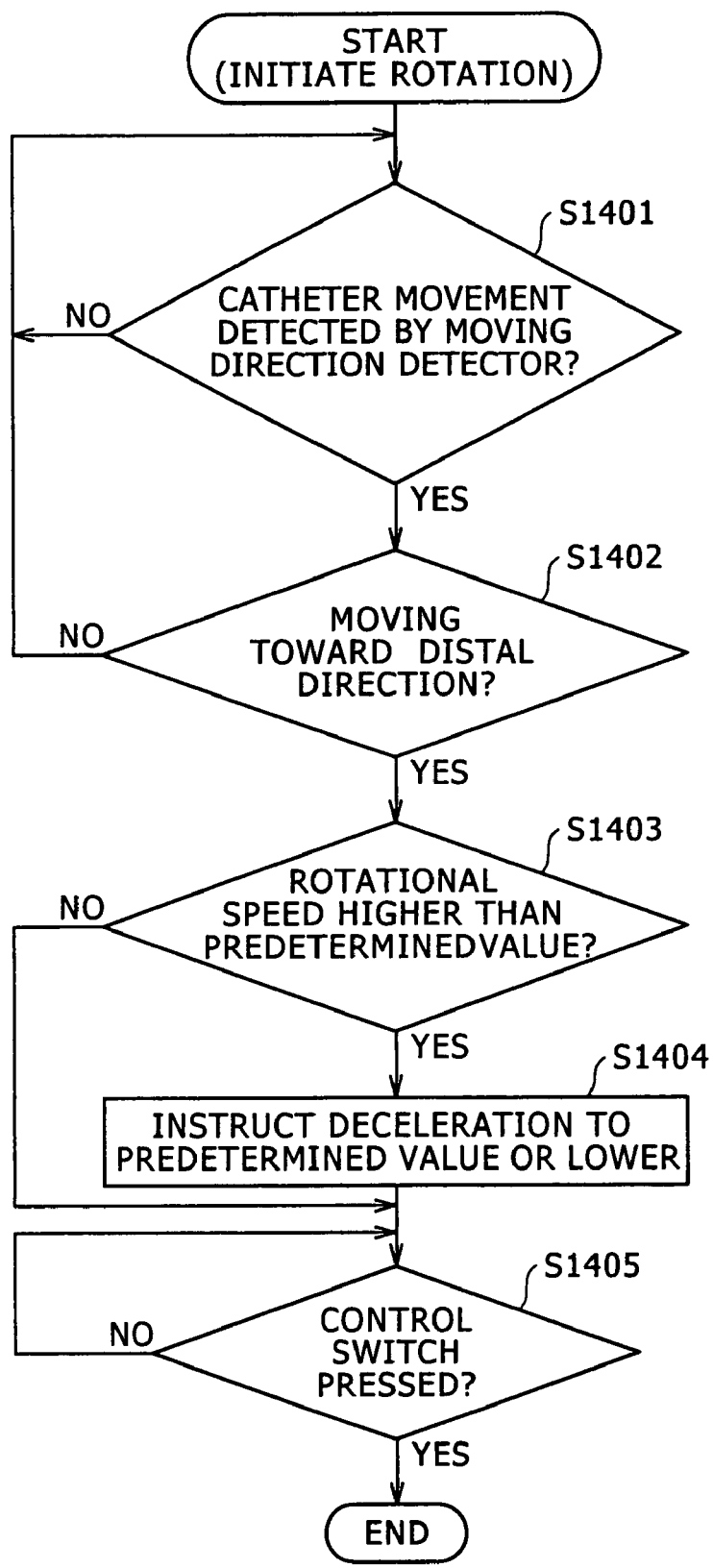
FIG. 14 is a flow chart showing operational aspects of the processing at a signal processor when an optical probe has initiated rotation.

When the optical probe 1201 initiates rotation at a predetermined rotational speed, the processing shown in FIG. 14 is started. The flow chart shown in FIG. 14 illustrates operational aspects at the signal processor 1214 when the optical probe 1201 has initiated rotation.

When the processing is started responsive to the receipt of a press signal (button operation signal) from the scan start button 823, a determination is made on the basis of an output signal from the moving direction detector 1230 in step S1401 as to whether or not the optical probe 1201 has moved axially. If no axial movement is determined, the process remains in a stand-by condition until an axial movement is detected.

If an axial movement is determined in step S1401, the process advances to step S1402. In step S1402, a determination is made as to whether or not the axial movement is a movement toward the distal direction within the body cavity. If the axial movement is not determined to be a movement toward the distal direction within the body cavity (in other words, is determined to be a movement away from distally or in a direction other than towards the distal end), the process returns to step S1401.

On the other hand, if the axial movement is determined to be a movement toward the distal direction within the body cavity, the process advances to step S1403. In step S1403, it is determined whether or not the rotational speed of the optical probe 1201 is higher than a predetermined value. The rotational speed of the optical probe 1201 is determined by referring to a value preset via the control panel 112 before pressing the scan start button 823. As an alternative, it may also be determined based on an actually-measured value of the rotational speed as calculated on the basis of an output from the encoder 1206. It is to be assumed that the predetermined value is set, for example, at 1,800 rpm.

If the rotational speed of the optical probe 1201 is not determined to be higher than the predetermined value in step S1403, the process advances to step S1405. On the other hand, if the rotational speed is determined to be higher than the predetermined value, that is if the preset value of the rotational speed is set at a high speed (for example, 3,600 rpm), the process advances to step S1404, and a deceleration instruction is transmitted to the rotary drive unit 1204 via the motor control circuit 1225 such that the rotational speed is reduced to or lower than the predetermined value. Responsive to the receipt of the deceleration instruction, the rotary drive unit 1204 performs control such that the rotary speed of the optical probe 1201 is reduced to or lower than the predetermined value.

In step S1405, a determination is made as to whether or not another control button (dial) is pressed (turned). If no other control button (dial) is determined to be pressed (turned) in step S1405, the process remains in a stand-by condition until another control button (dial) is pressed (turned). If another control button (dial) is determined to be pressed (turned), the processing shown in FIG. 14 is ended.

If it is determined in step S1405, for example, that the advance button 821 has been pressed, the optical probe 1201 is moved again toward the distal direction. If the retract button 822 is determined to have been pressed, the optical probe 1201 is moved away from or opposite to the distal direction. If the scan start button 823 is determined to have been pressed, the rotational speed of the optical probe 1201 is caused to return to the preset rotational speed (the rotational speed higher than the predetermined value). When the scan stop button 824 is pressed, the rotation of the optical probe 1201 which is rotating at a rotational speed equal to or higher than the predetermined value is stopped.

As described above, the signal processor 1214 transmits to the rotary drive unit 1204 the deceleration instruction in step S1404 to reduce the rotational speed of the probe to or lower than the predetermined value. However, a stop instruction may be transmitted to stop the rotation instead.

As is apparent from description set forth above, the system and apparatus include means (e.g., signal processor 1214) for determining, when movement of the probe toward the distal direction is detected, whether the rotational speed of the probe is greater than a predetermined value, and for effecting appropriate control to reduce the rotational speed of the probe when the rotational speed of the probe is determined to be greater than the predetermined value when the probe is determined to be moving toward the distal direction.

The OCT imaging system according to this disclosed embodiment helps avoid the possibility of breakage of the catheter. That is, in the event the rotational speed of the probe is relatively high during radial scanning at a time when the probe is moved toward the distal direction, the rotational speed of the probe is decelerated to a speed at which there is less likelihood, or no likelihood, for the occurrence of a catheter breakage problem, or the rotation of the probe is stopped.

[Third Embodiment]

The second embodiment described above applies the subject matter disclosed herein to an OCT imaging system. However, the subject matter at issue here is not specifically limited to OCT imaging systems, but can also be applied to OCT imaging systems making use of a wavelength swept light source. The following description describes application of the disclosed subject matter to an OCT imaging system making use of a wavelength swept light source.

1. Measurement Principle of OCT Imaging System Making use of a Wavelength Swept Light Source Initially, a brief description is set forth of the measurement principle of the OCT imaging system making use of a wavelength swept light source. This OCT imaging system and the OCT imaging system described above as the second embodiment are basically the same in terms of the measurement principle as generally illustrated in FIGS. 10 and 11. The following description primarily discusses differences of this version of the OCT imaging system relative to the OCT imaging system described above as the second embodiment.

It is the light source that is different in measurement principle from the OCT imaging system described above as the second embodiment. First, these OCT imaging systems are different in terms of coherence length. More specifically, a light source capable of emitting low-coherence light of from 10 μm to 20 μm or so in coherence length is used as the light source in the OCT imaging system described above as the second embodiment. On the other hand, a light source capable of emitting coherence length of from 4 mm to 10 mm or so in coherence length is used as a light source in the OCT imaging system making use of a wavelength swept light source.

As a reason for the above-mentioned difference, the range of the examinable range in the direction of the depth of a biotissue is dependent on the movable range of the reference mirror in the OCT imaging system described above as the second embodiment, but is dependent on the coherence length in the OCT imaging system making use of a wavelength swept light source. To encompass the entire range in the direction of the depth of a biotissue such as a blood vessel, a light source having a relatively long coherence length is used in the OCT imaging system making use of a wavelength swept light source.

Another difference in the light sources resides in that in the case of the OCT imaging system making use of a wavelength swept light source, light beams having different wavelengths are continuously irradiated.

In the OCT imaging system according to the second embodiment described above, the extraction of reflected light from individual points in the direction of the depth of the biotissue is achieved by movements of the reference mirror, and the resolution in the direction of the depth of the measurement target is dependent on the coherence length of irradiated light.

In the OCT imaging system making use of a wavelength swept light source, on the other hand, light is irradiated while continuously varying its wavelength and the intensities of reflected light from individual points in the direction of the depth of the biotissue are determined based on differences in the frequency component of interference light.

Taking the frequency (the inverse of the wavelength) of scanning light as a time function represented by Equation 1 below, the intensity of interference light can generally be expressed by a time function represented by Equation 2.

$$f(t) = f_\alpha + \Delta f t \quad \text{(Equation 1)}$$

$$I(t) = A + B \cos(C \Delta x (f_\alpha + \Delta f t)) \quad \text{(Equation 2)}$$

where $\Delta x$: optical path difference between the reference light and the target light,
$\Delta f$: the rate of a change in frequency in unit time, and
A, B, C: constants.

As indicated by Equation 2, the frequency component in the time-dependent change in the intensity I(t) of reference light is expressed by the optical path difference $\Delta x$ and the rate $\Delta f$ of a change in frequency by frequency scanning. Accordingly, the intensity of interference light for each optical path difference can be determined provided that the frequency component of the interference light is known.

As a consequence, the time required for acquiring signals for one line can be shortened, and further the imaging depth can be made greater.

Figure 15:
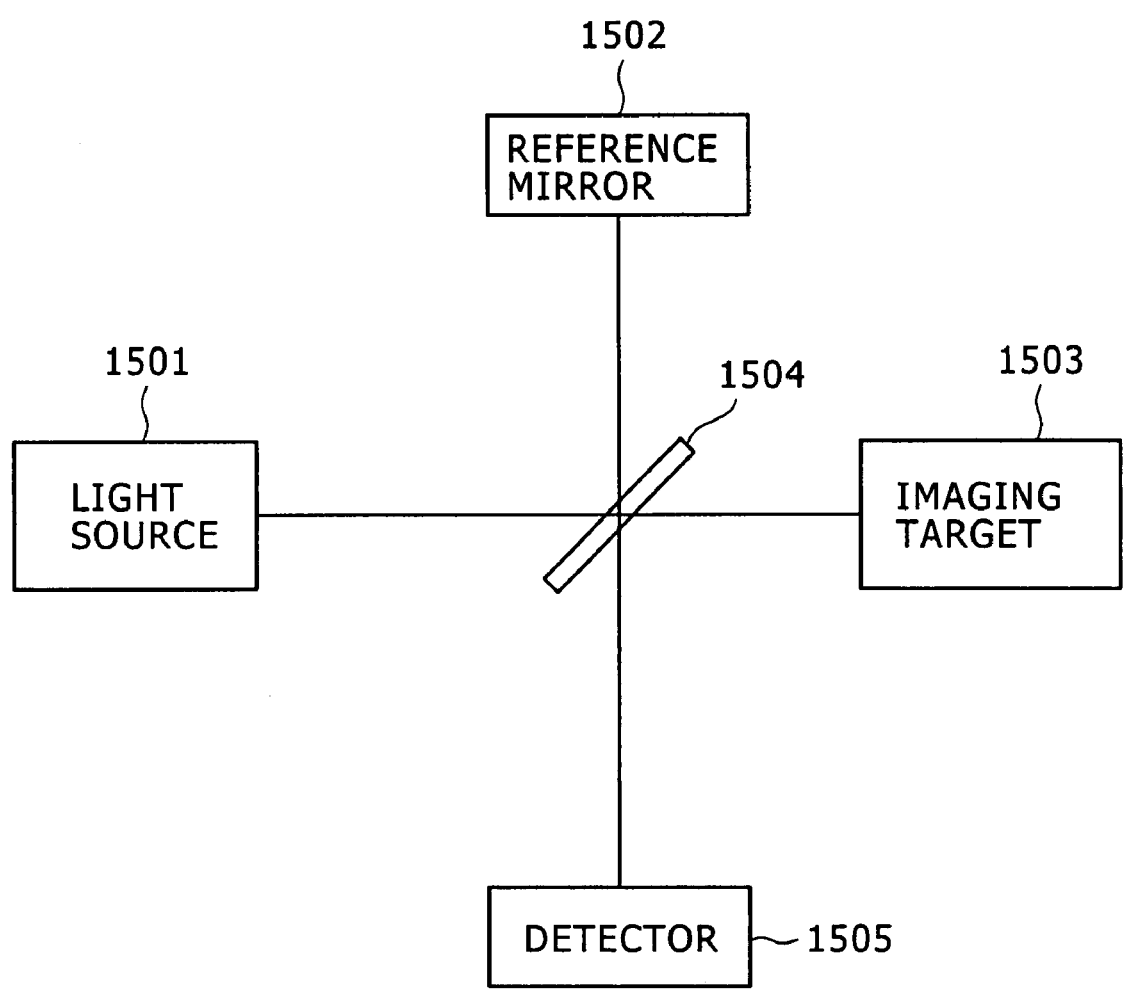
FIG. 15 is a block diagram illustrating the basic principle of an OCT imaging system according to a third embodiment which makes use of a wavelength swept light source.

As example of the basic principle of an OCT imaging system making use of a wavelength swept light source is shown in FIG. 15 which depicts the light source 1501 as a swept laser.

Light beams, which have been successively outputted from the light source 1501 and have different wavelengths, are each split at a beam splitter 1504, and the thus-split light beams then travel toward a reference mirror 1502 and an imaging target 1503, respectively. At this time, reflected light which is returning from the side of the imaging target 1503 includes light reflected on the surface of the imaging target, light reflected at shallow points in the imaging target, and light reflected at deep points in the imaging target.

By subjecting observed reference light to frequency resolution at a detector 1505 as mentioned above, information on a structure at a particular position in the direction of the depth of the measuring target can be visualized. As a result, a tomographic image can be formed.

As the light outputted from the light source 1501 is of from 4 to 10 mm or so in coherence length, it is possible to encompass the entire examination range in the direction of the depth of the imaging target. It is, therefore, unnecessary to move the reference mirror, so that the reference mirror 1502 is arranged fixedly at a constant distance. Moreover the reference mirror is not indispensable in this embodiment, a turned optical fiber, which can return back the light, may be set at the distal end of the reference optical path instead of the reference mirror.

Because it is unnecessary to mechanically move the reference mirror as mentioned above, the OCT imaging system making use of a wavelength swept light source, in comparison with the OCT imaging system according to the previously described second embodiment, requires a shorter time for acquiring signals for one line and can raise the frame rate. As opposed to a maximum frame rate of 15 fr/s (i.e., frames/second) in the OCT imaging system according to the second embodiment, the frame rate of the OCT imaging system making use of a wavelength swept light source is as high as from 30 to 200 fr/s or so.

In the case of an OCT imaging system irrespective of whether or not it makes use of a wavelength swept light source, blood is supposed to be eliminated upon diagnosis so that absorption of light by blood cell components can be avoided to acquire good images. A low frame rate, therefore, requires the elimination of blood for a longer time. This, however, leads to problems from the clinical standpoint. In the case of an OCT imaging system making use of frequency scanning, images can be acquired over 30 mm or longer in the axial direction of a blood vessel by elimination of blood for several seconds, thereby reducing such clinical problems.

Figure 16:
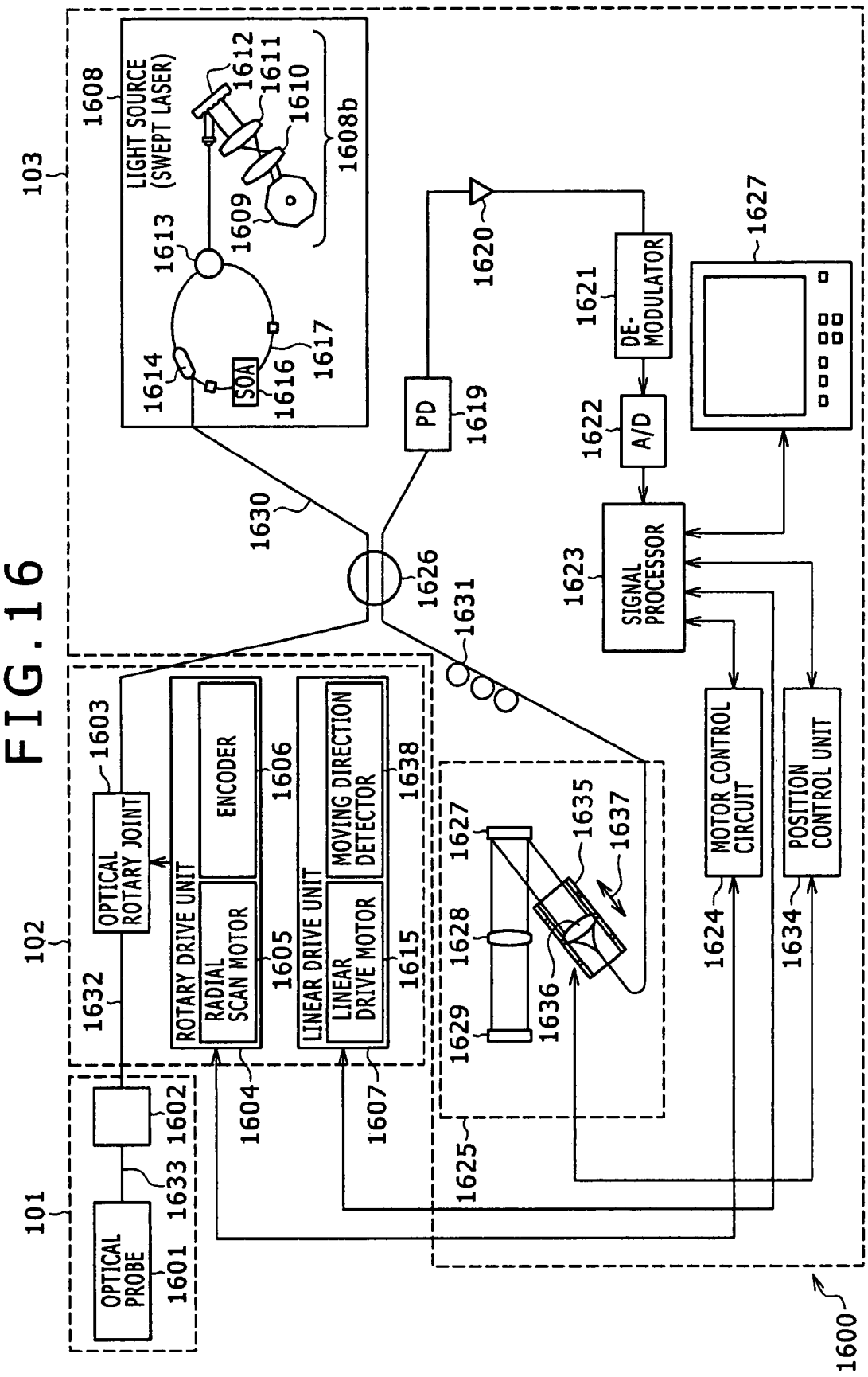
FIG. 16 is a block diagram depicting the functional construction of the OCT imaging system making use of a wavelength swept light source.

2. Aspects and Features of OCT Imaging System Making use of a Wavelength Swept Light Source Aspects and features of the OCT imaging system 1600 making use of a wavelength swept light source are schematically shown in FIG. 16. The description which follows primarily describes differences in the OCT imaging system 1600 making use of a wavelength swept light source relative to the OCT imaging system described above as the second embodiment with reference to FIG. 12.

The OCT imaging system 1600 making use of a wavelength swept light source includes a light source 1608. In the disclosed embodiment, a swept laser is used as the light source 1608. This swept laser 1608 is a kind of extended-cavity laser which comprises an optical fiber 1617 and a polygon scanning filter 1608*b*. The optical fiber 1617 is connected in the form of a ring with a semiconductor optical amplifier (SOA) 1616.

Light outputted from the SOA 1616 advances through the optical fiber 1617 and enters the polygon scanning filter 1608*b*. Subsequent to wavelength selection through the polygon scanning filter 1608*b*, the resulting light is amplified at the SOA 1616 and is finally outputted from a coupler 1614.

The polygon scanning filter 1608*b* selects a wavelength by a combination of a diffraction grating 1612, which separates light into a spectrum, and a polygon mirror 1609. The light, which has been separated into the spectrum by the diffraction grating 1612, is condensed on a facet of the polygon mirror 1609 by two lenses (1610, 1611). As a result, only light of a wavelength crossing at a right angle with the polygon mirror 1609 returns on the same light path and is outputted from the polygon scanning filter 1608*b*. By rotating the mirror, time sweeping of wavelengths is performed.

As an example of the polygon mirror 1609, a 32-sided polygonal mirror can be used, and its rotational speed can be 50,000 rpm or so. By the unique wavelength sweep system making the combined use of the polygon mirror 1609 and the diffraction grating 1612, high-speed and high-output wavelength sweep is feasible.

The light of the swept laser 1608, which has been outputted from the coupler 1614, impinges on the proximal end of a first single mode fiber 1630 and is transmitted toward its distal end face. At an optical coupler 1626 arranged midway along the first single mode fiber 1630, the first single mode fiber 1630 is optically coupled with a second single mode fiber 1631. Therefore, the light transmitted through the first single mode fiber 1630 is split into two by the optical coupler 1626 and the resulting two beams of light are transmitted further.

On the more distal end side of the first single mode fiber 1630 than the optical coupler 1626, an optical rotary joint 1603 is arranged to connect a non-rotatable block and a rotatable block with each other such that light can be transmitted.

Further, an optical-probe connector 1602 of the optical probe 1601 is detachably connected to the distal end of a third single mode fiber 1632 in the optical rotary joint 1603. Via the connector 1602, the light from the light source 1608 is transmitted to a fourth single mode fiber 1633 which is inserted in an optical probe 1601 and is rotationally drivable.

The transmitted light is irradiated from a distal end side of the optical probe 1601 toward a surrounding biotissue of a body cavity while performing radial scanning. A portion of reflected light scattered on a surface or interior of the biotissue is collected by the optical probe 1601, and returns toward the first single mode fiber 1630 through the reverse optical path. A portion of the thus-collected, reflected light is transferred by the optical coupler 1626 to the second single mode fiber 1631 and is introduced into a photodetector (for example, photodiode 1619) from an end of the second single mode fiber 1631. It is to be noted that the rotatable block side of the optical rotary joint 1603 is rotationally driven by a radial scan motor 1605 of the rotary drive unit 1604. Further, rotation angles of the radial scan motor 1605 are detected by an encoder 1606. The optical rotary joint 1603 is provided with a linear drive unit 1607 which, based on an instruction from a signal processor 1623, controls movement of the catheter section 101 in the direction of its insertion (in the axial direction). An axial movement is realized by an operation of a linear drive motor 1615 on the basis of a control signal from the signal processor 1623. Further, the moving direction of the catheter section 101 in its axial movement (toward or away from distally within the body cavity) is detected by a moving direction detector 1638, and the result of the detection is inputted to the signal processor 1623.

It is to be noted that the radial scan motor 1605 and the linear drive motor 1615 may be detachably connected together or may be integrally constructed. Axial movements by the linear drive motor 1615 can be realized by a ball screw or the like. Further, the moving direction detector 1638 can be realized, for example, by mounting an encoder on the linear drive motor 1615. Namely, the moving direction of the catheter section 101 in its axial movement can be detected by detecting the direction of rotation of the linear drive motor 1615.

On the more distal end side of the second single mode fiber 1631 than the optical coupler 1626, an optical path length (OPL) varying mechanism 1625 is arranged to finely adjust the optical path length of reference light.

This OPL varying mechanism 1625 is provided with a an OPL varying means for varying the optical path length by a length equivalent to a variation in the length of a new optical probe to absorb the variation when the new optical probe is used as a replacement.

The second single mode fiber 1631 and a collimator lens 1636 are mounted on a single axis stage 1635 movable in the direction of an optical axis of the collimator lens 1636 as indicated by an arrow 1637, thereby forming the OPL varying mechanism.

More specifically, the single axis stage 1635 forms the OPL varying mechanism having a variable OPL range just enough to absorb a variation in the optical path length of a new optical probe when the optical probe 1601 is replaced by the new optical probe. In addition, the single axis stage 1635 is also equipped with a function as an adjustment means for adjusting an offset. Even when the distal end of the optical probe 1601 is not in close contact with a surface of the biotissue, for example, the optical probe can still be set in such a state as interfering from a position on the surface of the biotissue by slightly varying the optical path length with the single axis stage 1635.

The light finely adjusted in optical path length by the OPL varying mechanism 1625 is combined with the light, which has escaped from the side of the first single mode fiber 1630, at the optical coupler 1626 arranged midway along the second single mode fiber 1631, and the combined light is received at the photodiode 1619.

The light received at the photodiode 1619 is photoelectrically converted, amplified by an amplifier 1620, and then inputted into a demodulator 1621. At the demodulator 1621, demodulation processing is performed to extract only the signal portion of the interfered light, and the output of the demodulator 1621 is inputted into an A/D converter 1622.

At the A/D converter 1622, interference light signals are sampled at 180 MHz as much as for 2,048 points to produce digital data (interference light data) for one line. It is to be noted that the setting of the sampling frequency at 180 MHz is attributed to the premise that approximately 90% of the cycle of wavelength sweep (12.5 μsec) be extracted as digital data at 2,048 points when the wavelength sweep repetition frequency is set at 40 kHz. The sampling frequency should be understood, therefore, not to be limited specifically to the above-described value.

The interference light data in line unit, which have been produced at the A/D converter 1622, are inputted into a signal processor 1623. At this signal processor 1623, the interference light data are frequency-resolved by FFT (Fast Fourier Transform) to produce data in the direction of the depth. These data are then coordinate-transformed to construct tomographic images at respective positions in the blood vessel. The tomographic images are then outputted at a predetermined frame rate to an LCD monitor 1627.

It is to be noted that the signal processor 1623 is connected with a position control unit 1634. The signal processor 1623 performs control of the position of the single axis stage 1635 via the position control unit 1634. In addition, the signal processor 1623 is also connected with a motor control circuit 1624, and in synchronization with video synchronization signals upon formation of tomographic images, stores the tomographic images in its internal memory.

The video synchronization signals from the motor control circuit 1624 are also sent to the rotary drive unit 1604, and the rotary drive unit 1604 outputs drive signals in synchronization with the video synchronization signals.

3. Construction of Catheter Section

The overall construction of the catheter section 101 and the construction of the distal end portion of the catheter are similar to those of the catheter and catheter section in the OCT imaging device described above as the second embodiment with reference to FIG. 13. Thus, a detailed description of the features of the catheter section is not repeated.

4. Features of Signal Processor 1623

Figure 17:
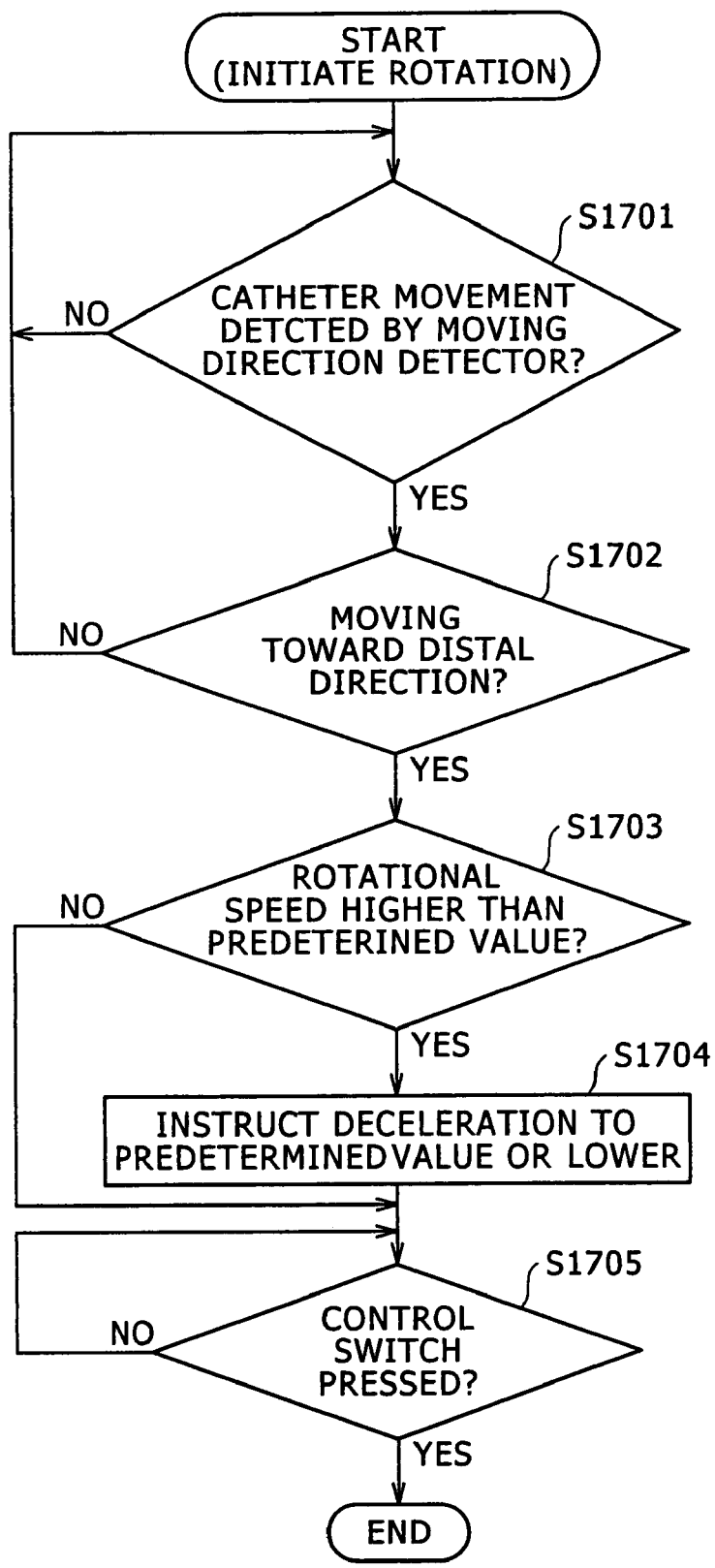
FIG. 17 is a flow chart showing operational aspects of the processing at a signal processor when an optical probe has initiated rotation.

When the optical probe 1601 initiates rotation at a predetermined rotational speed, the flow chart shown in FIG. 17 is started. The flow chart shown in FIG. 17 illustrates operational aspects of the signal processor 1623 when the optical probe 1601 has initiated rotation.

When the processing is started responsive to the receipt of a press signal from the scan start button 823, a determination is made on the basis of an output signal from the moving direction detector 1638 in step S1701 as to whether or not the optical probe 1601 has moved axially. If no axial movement is determined, the process remains in a stand-by condition until an axial movement is detected.

If an axial movement is determined in step S1701, the process advances to step S1702. In step S1702, a determination is made as to whether or not the axial movement is a movement toward the distal direction within the body cavity. If the axial movement is not determined to be a movement toward the distal direction within the body cavity (in other words, is determined to be a movement away from or opposite to the distal direction), the process returns to step S1701.

If the axial movement is determined to be a movement toward the distal direction within the body cavity in step SI 702, the process advances to step S1703. In step S1703, it is determined whether or not the rotational speed of the optical probe 1601 is higher than a predetermined value. The rotational speed of the optical probe 1601 is determined by referring to a value preset via the control panel 112 before pressing the scan start button 823. As an alternative, it may also be determined based on an actually-measured value of the rotational speed as calculated on the basis of an output from the encoder 1606. It is to be assumed that the predetermined value is set, for example, at 1,800 rpm.

If the rotational speed of the optical probe 1601 is not determined to be higher than the predetermined value in step S1703, the process advances to step S1705. If the rotational speed is determined to be or higher than the predetermined value, on the other hand, that is, if the preset value of the rotational speed is set at a high speed (for example, 3,600 rpm), the process advances to step S1704, and a deceleration instruction is transmitted to the rotary drive unit 1604 via the motor control circuit 1624 such that the rotational speed is reduced to or lower than the predetermined value. Responsive to the receipt of the deceleration instruction, the rotary drive unit 1604 performs control such that the rotary speed of the optical probe 1601 is reduced to or lower than the predetermined value.

In step S1705, a determination is made as to whether or not another control button (dial) is pressed (turned). If no other control button (dial) is determined to be pressed (turned) in step S1705, the process remains standing by until another control button (dial) is pressed (turned). If another control button (dial) is determined to be pressed (turned), on the other hand, the processing shown in FIG. 17 is ended.

If it is determined in step S1705, for example, that the advance button 821 has been pressed, the optical probe 1601 is moved again toward the distal direction. If the retract button 822 is determined to have been pressed, the optical probe 1601 is moved away from or opposite to the distal direction. If the scan start button 823 is determined to have been pressed, the rotational speed of the optical probe 1601 is caused to return to the preset rotational speed (the rotational speed higher than the predetermined value). When the scan stop button 824 is pressed, the rotation of the optical probe 1601 which is rotating at a rotational speed equal to or higher than the predetermined value is stopped.

In the above description, the signal processor 1623 transmits to the rotary drive unit 1604 the deceleration instruction in step S1704 such that the rotational speed is reduced to or lower than the predetermined value. However, a stop instruction may instead be transmitted to stop the rotation.

From the above-description, it is understood that the system and apparatus include means (e.g., signal processor 1623) for determining, when movement of the probe toward the distal direction is detected, whether the rotational speed of the probe is greater than a predetermined value, and for effecting appropriate control to reduce the rotational speed of the probe when the rotational speed of the probe is determined to be greater than the predetermined value when the probe is determined to be moving toward the distal direction.

The OCT imaging system making use of a wavelength swept light source according to this embodiment helps avoid the possibility of breakage of the catheter. That is, in the event the rotational speed of the probe is relatively high during radial scanning at a time when the probe is moved toward the distal direction, the rotational speed of the probe is decelerated to a speed at which there is less likelihood, or no likelihood, for the occurrence of a catheter breakage problem, or the rotation of the probe is stopped.

The principles, preferred embodiments and modes of operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An image diagnostic system comprising:
   a probe positionable in a body cavity and configured to repeatedly transmit signals into the body cavity and receive reflected signals which are reflected by biotissue surrounding the body cavity;
   a rotational scanning unit connected to the probe and configured to rotate the probe to perform a rotational scan;
   an axial-moving unit connected to the probe to axially move the probe; and
   a control unit configured to produce data based on the reflected signals to construct a tomographic image of the body cavity and surrounding biotissue, the control unit comprising:
   a detection unit configured to detect an axial direction of movement of the probe;
   a rotational scan controller connected to the rotational scanning unit and configured to control the rotational scanning unit to rotate the probe at a rotational speed;
   the rotational scan controller controlling the rotational scanning unit to change the rotational speed of the probe upon an output from the detection unit;
   a determination unit configured to determine whether or not the rotational speed of the probe is to be changed upon detection of a movement of the probe toward a distal direction by the detection unit; and
   the determination unit making a determination to reduce the rotational speed of the probe when the detection unit detects movement of the probe toward the distal direction within the body cavity at a time when the rotational speed of the probe is higher than a predetermined value.

2. The image diagnostic system according to claim 1, wherein the rotational scan controller reduces the rotational speed of the probe when the detection unit detects movement of the probe toward a distal direction.

3. The image diagnostic system according to claim 1, wherein the rotational scan controller controls the rotational scanning unit to stop rotation of the probe when the detection unit detects that the probe moves toward a distal direction.

4. The image diagnostic system according to claim 1, wherein when the detection unit detects movement of the probe toward the distal direction at a time when the rotational speed of the probe is higher than the predetermined value, the rotational scan controller controls the rotational scanning unit to reduce the rotational speed of the probe at least to the predetermined value.

5. The image diagnostic system according to claim 1, wherein when the detection unit detects movement of the probe toward the distal direction at a time when the rotational speed of the probe is higher than the predetermined value, the rotational scan controller controls the rotational scanning unit to stop rotation of the probe.

6. The image diagnostic system according to claim 1, wherein the probe is adapted to be connected to a light source which outputs light, with the probe being configured to transmit and receive the light, and the data are produced based on interference light between light reflected in the body cavity and received through the probe and a reference light split from the light outputted from the light source.

7. The image diagnostic system according to claim 1, wherein the probe comprises an ultrasonic transducer which transmits and receives ultrasounds, and the data is produced by the control unit based on ultrasound waves reflected in the body cavity and received through the probe.

8. An image diagnostic system comprising:
   a probe positionable in a body cavity and configured to repeatedly transmit signals into the body cavity and receive reflected signals which are reflected by biotissue surrounding the body cavity;
   a radial scan motor connected to the probe to rotate the probe to perform rotational scanning;
   a linear drive motor connected to the probe to axially move the probe toward a distal direction;
   a control unit configured to produce data based on the reflected signals to construct a tomographic image of the body cavity and surrounding biotissue, the control unit comprising:
   a detection unit configured to detect an axial direction of movement of the probe; and
   means for determining, when the detection unit detects movement of the probe toward the distal direction, whether a rotational speed of the probe is greater than a predetermined value, and for controlling the radial scan motor to reduce the rotational speed of the probe when the rotational speed of the probe is determined to be greater than the predetermined value when the detection unit detects movement of the probe toward the distal direction.

9. An image diagnostic apparatus for controlling a probe, which is adapted to be connected to the image diagnostic apparatus and to repeatedly transmit signals into a body cavity which are reflected by biotissue surrounding the body cavity to perform radial scanning within the body cavity, the image diagnostic apparatus comprising:
   a rotational scanning unit connectable to the probe and configured to rotate the probe to perform a rotational scan;
   an axial-moving unit connectable to the probe to axially move the probe; and
   a control unit configured to produce data based on the reflected signals to construct a tomographic image of the body cavity and surrounding biotissue;
   the control unit comprising:
   a detection unit configured to detect an axial direction of movement of the probe;
   a rotational scan controller connected to the rotational scanning unit and configured to control the rotational scanning unit to rotate the probe at a rotational speed;

the rotational scan controller controlling the rotational scanning unit to change the rotational speed of the probe upon an output from the detection unit;

a determination unit configured to determine whether or not the rotational speed of the probe is to be changed upon detection of a movement of the probe toward a distal direction by the detection unit; and the determination unit making a determination to reduce the rotational speed of the probe when the detection unit detects movement of the probe toward a distal direction within the body cavity at a time when the rotational speed of the probe is higher than a predetermined value.

10. The image diagnostic apparatus according to claim 9, wherein the rotational scan controller controls the rotational scanning unit to reduce the rotational speed of the probe when the detection unit detects movement of the probe toward a distal direction.

11. The image diagnostic apparatus according to claim 9, wherein the rotational scan controller controls the rotational scanning unit to stop rotation of the probe when the detection unit detects that the probe moves toward a distal direction.

12. The image diagnostic apparatus according to claim 9, wherein when the detection unit detects movement of the probe toward the distal direction at a time when the rotational speed of the probe is higher than the predetermined value, the rotational scan controller controls the rotational scanning unit to reduce the rotational speed of the probe at least to the predetermined value.

13. The image diagnostic apparatus according to claim 9, wherein when the detection unit detects movement of the probe toward the distal direction at a time when the rotational speed of the probe is higher than the predetermined value, the rotational scan controller controls the rotational scanning unit to stop rotation of the probe.

14. The image diagnostic apparatus according to claim 9, wherein the probe to which the image diagnostic apparatus is adapted to be connected is connected to a light source which outputs light, with the probe being configured to transmit and receive the light, and the data are produced based on interference light between light reflected in the body cavity and received through the probe and a reference light split from the light outputted from the light source.

15. The image diagnostic apparatus according to claim 9, wherein the probe to which the image diagnostic apparatus is adapted to be connected comprises an ultrasonic transducer which transmits and receives ultrasounds, and the data is produced by the control unit based on ultrasound waves reflected in the body cavity and received through the probe.

16. A method for controlling, in an image diagnostic system, an axially and rotationally movable probe which repeatedly transmits signals within a body cavity and receives signals reflected in the body cavity during rotational scanning, with the signals received by the probe being used to form and output tomographic images of the body cavity and biotissue surrounding the body cavity, the method comprising:

determining a direction of axial movement of the probe during rotational scanning;

changing a rotational speed of the probe when the probe is determined to be moving toward a distal direction within the body cavity; and determining whether the rotational speed of the probe is greater than a predetermined value when the probe is determined to be moving toward the distal direction within the body cavity, and reducing the rotational speed of the probe when the rotational speed of the probe is determined to be greater than the predetermined value and when the probe is determined to be moving toward the distal direction within the body cavity.

17. The method according to claim 16, wherein the changing of the rotational speed of the probe comprises reducing the rotational speed of the probe when the probe is determined to be moving toward the distal direction within the body cavity.

18. The method according to claim 16, wherein the changing of the rotational speed of the probe comprises stopping the rotation of the probe when the probe is determined to be moving toward the distal direction within the body cavity.

19. A non-transitory recording medium with a control program stored therein for performing by a computer an information processing method according to claim 16.

20. An image diagnostic system comprising:

a probe positionable in a body cavity and configured to repeatedly transmit signals into the body cavity and receive reflected signals which are reflected by biotissue surrounding the body cavity;

a rotational scanning unit connected to the probe and configured to rotate the probe to perform a rotational scan;

an axial-moving unit connected to the probe to axially move the probe; and a control unit configured to produce data based on the reflected signals to construct a tomographic image of the body cavity and surrounding biotissue, the control unit comprising:

a detection unit configured to detect an axial direction of movement of the probe;

a rotational scan controller connected to the rotational scanning unit and configured to control the rotational scanning unit to rotate the probe at a rotational speed;

the rotational scan controller controlling the rotational scanning unit to change the rotational seed of the probe upon an output from the detection unit; and wherein whenever the detection unit detects the probe is moving in a distal axial direction, if the rotational speed of the probe exceeds a predetermined rotational speed, the rotational scan controller reduces the rotational speed of the probe but continues to rotate the probe.

* * * * *